United States Patent
Verkman et al.

(10) Patent No.: US 7,638,543 B2
(45) Date of Patent: *Dec. 29, 2009

(54) CYSTIC FIBROSIS TRANSMEMBRANE CONDUCTANCE REGULATOR PROTEIN INHIBITORS AND USES THEREOF

(75) Inventors: Alan Verkman, San Francisco, CA (US); Tonghui Ma, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/761,295

(22) Filed: Jun. 11, 2007

(65) Prior Publication Data

US 2008/0064666 A1     Mar. 13, 2008

Related U.S. Application Data

(63) Continuation of application No. 10/676,727, filed on Sep. 30, 2003, now Pat. No. 7,235,573.

(60) Provisional application No. 60/509,049, filed on Sep. 30, 2002, provisional application No. 60/480,253, filed on Jun. 20, 2003.

(51) Int. Cl.
    *A61K 31/426* (2006.01)
(52) U.S. Cl. .................................... 514/369
(58) Field of Classification Search ................. None
    See application file for complete search history.

(56) References Cited

U.S. PATENT DOCUMENTS

| | | | | |
|---|---|---|---|---|
| 4,873,255 | A * | 10/1989 | Yoshioka et al. | 514/369 |
| 4,965,155 | A | 10/1990 | Nishiguchi et al. | 430/58 |
| 5,856,331 | A | 1/1999 | Bursten et al. | 514/263 |
| 6,380,186 | B1 | 4/2002 | Howard | 514/227.8 |
| 6,403,592 | B1 | 6/2002 | Howard | 514/254.02 |
| 6,423,708 | B1 | 7/2002 | Gibbs et al. | 514/227.8 |
| 2002/0049211 | A1 | 4/2002 | Sobolov-Jaynes et al. | 514/250 |
| 2002/0049214 | A1 | 4/2002 | Gibbs et al. | 514/253.01 |
| 2002/0052396 | A1 | 5/2002 | Bailey et al. | 514/369 |
| 2002/0072519 | A1 | 6/2002 | Howard | 514/218 |
| 2002/0091117 | A1 | 7/2002 | Howard | 514/212.03 |
| 2002/0091118 | A1 | 7/2002 | Howard | 514/212.03 |
| 2002/0091119 | A1 | 7/2002 | Howard | 514/212.03 |

FOREIGN PATENT DOCUMENTS

| EP | 0434394 B1 | 8/1998 |
|---|---|---|
| JP | 1-156752 A | 6/1989 |
| JP | 1-172836 A | 7/1989 |
| JP | 1-173065 A | 7/1989 |

OTHER PUBLICATIONS

Ma et al., "Thiazolidinone CFTR inhibitor identified by high-throughput screening blocks cholera toxin-induced intestinal fluid secretion," *The Journal of Clinical Investigation* 110(11): 1651-1658, Dec. 2002.

Abdel-Rahman et al., "Heterodiene Synthesis. I Reaction of 5-Arylidenerhodanine Derivatives with 1-Morpholinocyclohexene Enamine," *Synthetic Communications* 19(3&4): 345-354, 1989.

Abdel-Rahman et al., "A Chemical Evidence Supporting the Formation of Dihydropyran Adducts from the Reaction of 5-Arylidenerhodanines with 1-Morpholoncyclohexene through Zwitterionic Intermediate," *Afinidad L.* 50(445): 155-159, 1993.

Adbel-Rahman, "Dihydopyrans from the Heterodienic Reaction of 5-Arylidenerhodanine Derivatives with Isoprene," *Chem. Papers* 47(6): 385-387, 1993.

Cabantchik et al., "Chemical probes for anion transporters of mammalian cell membranes," Invited Review, *The American Physiological Society*, pp. C803-C827, 1992.

Edwards et al., "Induction of a glibenclamide-sensitive K-current by modification of a delayed rectifier channel in rat portal vein and insulinoma cells," *Br. J. Pharmacol* 110: 1280-1281, 1993.

(Continued)

*Primary Examiner*—Patricia A Duffy
*Assistant Examiner*—Anna Pagonakis
(74) *Attorney, Agent, or Firm*—Seed IP Law Group PLLC

(57) ABSTRACT

The invention provides compositions, pharmaceutical preparations and methods for inhibition of cystic fibrosis transmembrane conductance regulator protein (CFTR) that are useful for the study and treatment of CFTR-mediated diseases and conditions. The compositions and pharmaceutical preparations of the invention may comprise one or more thiazolidinone compounds, and may additionally comprise one or more pharmaceutically acceptable carriers, excipients and/or adjuvants. The methods of the invention comprise, in certain embodiments, administering to a patient suffering from a CFTR-mediated disease or condition, an efficacious amount of a thiazolidinone compound. In other embodiments the invention provides methods of inhibiting CFTR that comprise contacting cells in a subject with an effective amount of a thiazolidinone compound. In addition, the invention features a non-human animal model of CFTR-mediated disease which model is produced by administration of a thiazolidinone compound to a non-human animal in an amount sufficient to inhibit CFTR.

13 Claims, 23 Drawing Sheets

OTHER PUBLICATIONS

El-Shafei et al., "Applications of Phase-Transfer Catalysis in Reactions with Rhodanine Derivatives," *Gazzetta Chimica Italiana 120*: 197-201, 1990.

Gabriel et al., "Cystic Fibrosis Heterozygote Resistance to Cholera Toxin in the Cystic Fibrosis Mouse Model," *Science 266*:107-109, Oct. 7, 1994.

Gabriel et al., "A novel plant-derived inhibitor of cAMP-mediated fluid and chloride secretion," *The American Physiology Society*, pp. G58-G63, 1999.

Galietta et al., "Novel CFTR Chloride Channel Activators Identified by Screening of Combinatorial Libraries Based on Flavone and Benzoquinolizinium Lead Compounds," *J. Biological Chemistry 276*(23): 19723-19728, Jun. 8, 2001.

Gorbach et al., "Acute Undifferentiated Human Diarrhea in the Tropics," *The Journal of Clinical Investigations 50*: 881-889, 1971.

Grubb et al., "Pathophysiology of Gene-Targeted Mouse Models for Cystic Fibrosis," *Physiology Reviews 79*: Suppl. S193-S214, Jan. 1999.

Gupta et al., "Synthesis and Fungitoxicity of Some 5-Substituted-3-Polynitrophenyl Rhodanines," *J. Indian Chem. Soc. LV*: 483-485, May 1978.

Hongre et al., "Effects of sulphonyllureas on cAMP-stimulated Cl transport via the cystic fibrosis gene product in human epithelial cells," *Pflügers Arch. 426*: 284-287, 1994.

Jayararnan et al., "Submucosal gland secretions in airways from cystic fibrosis patients have normal [$Na^+$] and pH but elevated viscosity," *PNAS 98*(14): 8119-8123, Jul. 3, 2001.

Khalil et al., "The Action of Arylamines on 3-Aryl-5-Arylmethylenerhodanines," *Revue Roumaine de Chirnie 23*(6): 935-941, 1978.

Khan et al., "Synthesis and insecticidal activity of 5-amino-7-arly-6-cyano-3-substituted-thiazolo[4,5-*b*]-2,3,4,7-tetrahydropyridine-2-thione and 7-aryl-cyano-3-substituted-2-thioxo-thiazolo [4,5-*b*]-2,3,4,5,6,7-hexahydropyridin-5-one," *Indian Journal of Chemistry 37B*: 1069-1074, Oct. 1998.

Ladnaya et al., "Synthesis and properties of Thiazolidons-4 Obtained From Phenamine II. Thiasolidindions-2,4," *Luov Medical Institute*, pp. 37-41, with English abstract, 1972.

Lohi et al., "Upregulation of CFTR expression but not SLC26A3 and SLC9A3 in ulcerative colitis," *Am J Physiol. Gastrointest. Liver Physiol. 283*: G567-G575, 2002.

Ma et al., *J. Biol. Chem. 277*(40): 37235-37241, Oct. 4, 2002. Originally published in Press as doi:10.1074/jbc, M205932200 on Aug. 2, 2002.

Ma et al., *The Journal of Clinical Investigation 110*(11): 1651-1658, Dec. 2002.

Makhlouf et al., "New antomicrobial rhodanines," *Pharmazie. 51*: 430-431, 1996.

McDonough et al., "Novel Pore-Lining Residues in CFTR That Govern Permeation and Open-Channel Block," *Neuron 13*: 623-634, Sep. 1994.

Noone et al., "CFTR-opathies': disease phenotypes associated with cystic fibrosis transmembrane regulator gene mutations," *Respir. Res. 2*: 328-332, 2001.

Oi et al., "Identification in traditional herbal medications and confirmation by synthesis of factors that inhibit cholera toxin-induced fluid accumulation," *PNAS 99*(5): 3042-3046, Mar. 5, 2002.

Omar et al., "The Role of Substituents at Postion-3 on the Mode of Cleavage of 5- Arylmethylene-2, 4-dioxothiazolidines," *Journal f. prakt. Chemie. Band 331, Heft 3*, S393-S398, 1989.

Pilewslci et al., "Role of CFTR in Airway Disease," *Physiological Review 79*(Suppl. 1): S215-S255, Jan. 1999.

Rabe et al., "$Cl^-$ channel inhibition by glibenclamide is not specific for the CFTR-type $Cl^-$ channel," *Pflügers Arch-Eur J. Physiol. 429*: 659-662, 1995.

Rasola et al., "Volume-sensitive Chloride Currents in Four Epithelial Cell Lines Are Not Directly Correlated to the Expression of the MDR-1 Gene," *J. Biol. Chem. 269*(2): 1432-1436, Jan. 14, 1994.

Richardson et al., "Studies on the Genetic and Cellular Control of Sensitivity to Enterotoxins in the Sealed Adult Mouse Model," *Infection and Immunity 54*(2): 522-528, Nov. 1986.

Schultz et al., "Pharmacology of CFTR Chloride Channel Activity," *Physiological Reviews 79*(Suppl. 1): S109-S144, Jan. 1999.

Sheppard et al., "Effect of ATP-sensitive $K^+$ Channel Regulators on Cystic Fibrosis Transmembrane Conductance Regulator Chloride Currents," *J. Gen. Physiol. 100*: 573-591, Oct. 1992.

Tejchman et al., "Introduction of Selenium to Heterocyclic Compounds. Part VII. Synthesis of 3-Alkyl-5-benzylidene- and 3-Alkyl-5-cinnamylidene-2-selenorhodanines," *Polish J. Chem. 73*: 1315-1322, 1999.

Tejchman et al., "Introduction of Selenium to Hetreocyclic Compounds. Part VI. Synthesis of 3-Arly-5-benzylidene- and 3-Aryl-5-cinnarnylidene-2-selenorhodanines," *Polish J. Chem. 70*: 1124-1134, 1996.

Tiwari et al., "Synthesis and fungicidal activity of some 3,7-diaryl-6-cyanorhodanino[4,5-*b*]-pyridin-5 (4*H*)-ones and 3-aryl-rhodanino[4,5-*b*]furan-6 (5*H*)-ones," *Indian Journal of Chemistry 28B*: 796-798, Sep. 1989.

Wong, "CFTR gene and male fertility," *Molecular Human Reproduction 4*(2): 107-110, 1998.

Yadav et al., "Synthesis and Fungitoxicity of Rationally Designed Thiazolo-1,3-dithiins, -thiazines, and -oxathiines," *J. Agric. Food Chem. 40*: 1214-1216, 1992.

Yamada et al., "Steric Hindrance of 2-Arylimino-3-aryl-4-thiazolidones" *Utsunomiya Daigaku Kyoikugakubu Kiyo 34*(2): 33-41, Dec. 1983.

Yamazaki et al., "Inhibitory Effects of Glibenclamide on Cystic Fibrosis Transmembrane Regulator, Swelling-Activated, and $Ca^{2+}$-Activated $Cl^-$ Channels in Mammalian Cardiac Myocytes," *Circulation Research 81*(1): 101-109, Jul. 1997.

Appendix C—Thiazolidinione Chemical Structure Search (Identified References), pp. 1-70, 2002.

Memorandum Regarding Compound Collections, Dated May 15, 2003.

Database HCAPLUS on STN Online, No. 2002:932809, Ma et al., "Thiazolidinone CFTR Inhibitor Identified by High-Throughput Screening Blocks Cholera Toxin-Induced Intestinal Fluid Secretion," abstract, *Journal of Clinical Investigation*, 2002, vol. 110, No. 11, pp. 1651-1658.

Database HCAPLUS on STN Online, No. 1978:597389, Gupta et al. "Synthesis and Fungitoxicity of some 5-substituted 3-poly(nitrophenyl) rhodanines," abstract, *Journal of the Indian Chemistry Society*, 1978, vol. 55, No. 5, pp. 483-485.

Database HCAPLUS on STN Online, No. 2002:664146, Roman et al. "Synthesis and Antiinflarnmatory Activity of 3-aryl-5-arylidene-thioxothiazolidine-4-ones," abstract, *Framatsevtichnii Zhurnal (Kiev)*, 2002, vol. 3, pp. 56-59.

Roman, O.M. et al., "Synthesis and anti-inflammatory activity of 3-aryl-5-arylidene-2-thixothiazolidine-4-ones," *Farmatsevtichnii Zhurnal (Kiev)* (3): 56-59, 2002.

Roman, O.M. et al., "Synthesis and anti-inflammatory activity of 3-aryl-5-arylidene-2-thioxothiazolidin-4-ones," *Farmatsevtichnii Zhurnal (Kiev)* (3): 56-59, 2002, English Translation.

Ladnaya et al., "Synthesis and properties of Thiazolidons-4 Obtained From Phenamine II. Thiasolidindions-2,4," *Luov Medical Institute*, pp. 37-41, with English abstract.

Ma et al., *J. Biol. Chem. 277*(40): 37235-37241, Oct. 4, 2002. Originally published in Press as doi:10.1074/jbc, M205932200 on Aug. 2, 2002.

Makhlouf et al., "New antomicrobial rhodanines," *Pharmazie. 51*: 430-431, 1996.

Noone et al., "'CFTR-opathiesi': disease phenotypes associated with cystic fibrosis transmembrane regulator gene mutations," *Respir. Res. 2*: 328-332, 2001.

Pilewski et al., "Role of CFTR in Airway Disease," *Physiological Review 79*(Suppl. 1): S215-S255, Jan. 1999.

* cited by examiner

CFTR$_{inh}$ -020

CFTR$_{inh}$ -029

CFTR$_{inh}$ -172

CFTR$_{inh}$ -185

CFTR$_{inh}$ -214

CFTR$_{inh}$ -236

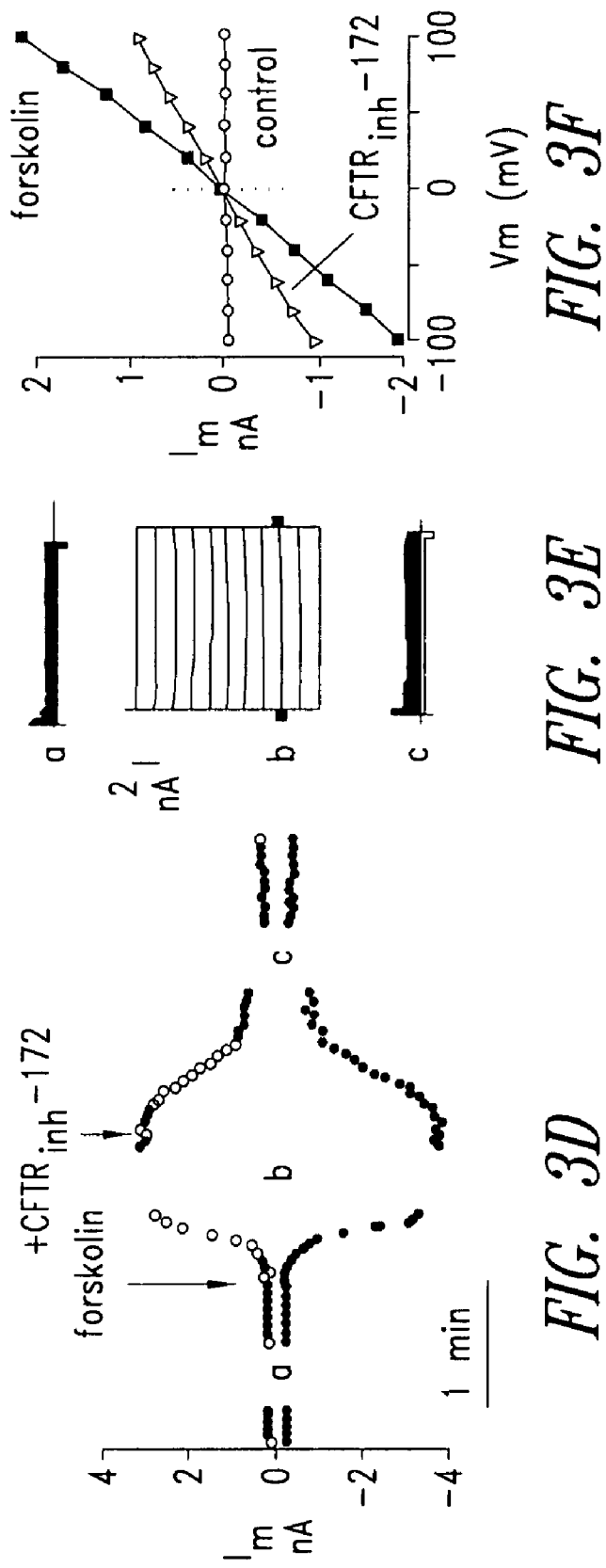

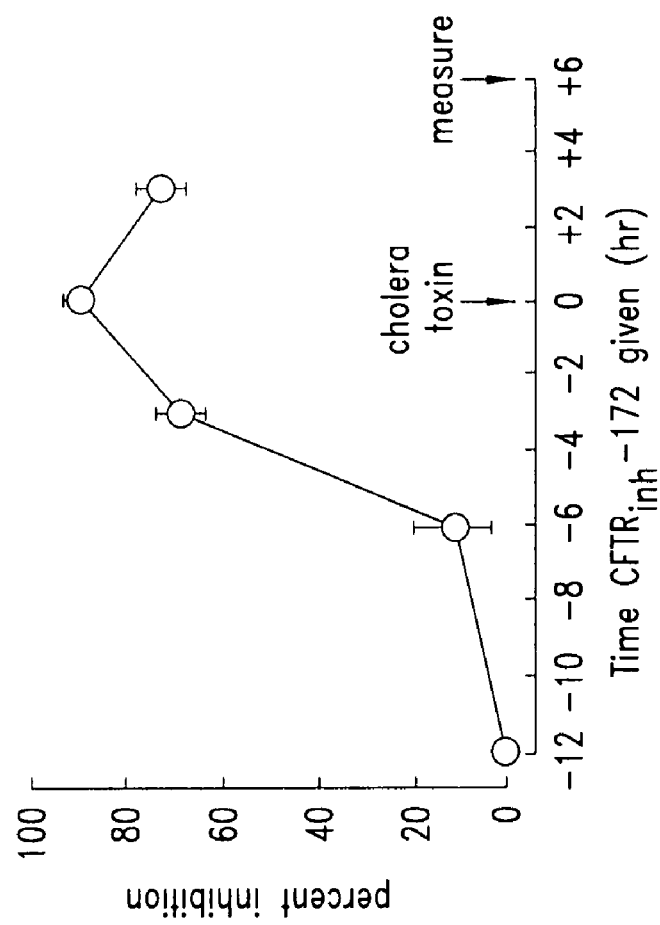
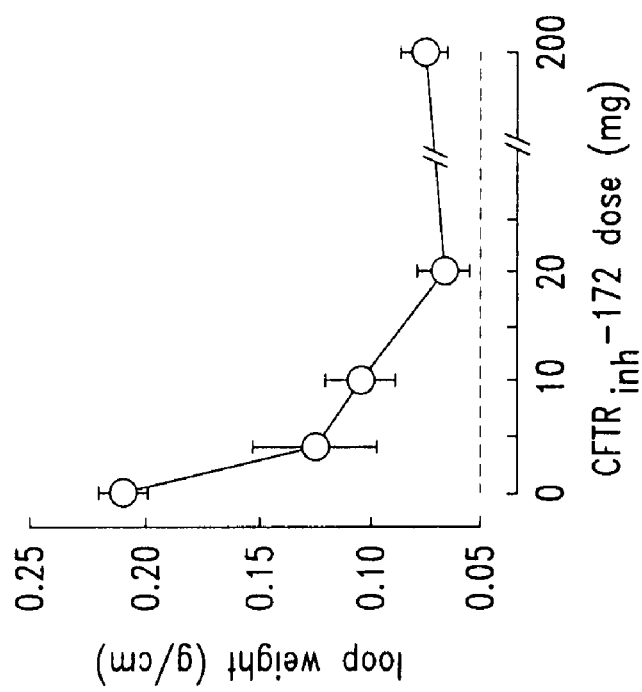
FIG. 11B
FIG. 11A

CYSTIC FIBROSIS TRANSMEMBRANE CONDUCTANCE REGULATOR PROTEIN INHIBITORS AND USES THEREOF

CROSS-REFERENCE TO RELATED APPLICATIONS

This application is a continuation of U.S. patent application Ser. No. 10/676,727 filed Sep. 30, 2003, now issued as U.S. Pat. No. 7,235,573 on Jun. 26, 2007, which claims the benefit of U.S. Provisional Application No. 60/509,049 filed Sep. 30, 2002 and U.S. Provisional Application No. 60/480,253 filed Jun. 20, 2003, all of which are incorporated herein by reference in their entireties.

STATEMENT OF GOVERNMENT INTEREST

This invention was made with government support under grants HL059198 and HL073856 awarded by National Institutes of Health. The government has certain rights in this invention.

BACKGROUND OF THE INVENTION

The cystic fibrosis transmembrane conductance regulator protein (CFTR) is a cAMP-activated chloride (Cl$^-$) channel expressed in epithelial cells in mammalian airways, intestine, pancreas and testis. CFTR is the chloride-channel responsible for cAMP-mediated Cl$^-$ secretion. Hormones, such as a β-adrenergic agonist, or a toxin, such as cholera toxin, leads to an increase in cAMP, activation of cAMP-dependent protein kinase, and phosphorylation of the CFTR Cl$^-$ channel, which causes the channel to open. An increase in cell Ca$^{2+}$ can also activate different apical membrane channels. Phosphorylation by protein kinase C can either open or shut Cl$^-$ channels in the apical membrane. CFTR is predominantly located in epithelia where it provides a pathway for the movement of Cl$^-$ ions across the apical membrane and a key point at which to regulate the rate of transepithelial salt and water transport. CFTR chloride channel function is associated with a wide spectrum of disease, including cystic fibrosis (CF) and with some forms of male infertility, polycystic kidney disease and secretory diarrhea.

The hereditary lethal disease cystic fibrosis (CF) is caused by mutations in CFTR. Observations in human cystic fibrosis (CF) patients and CF mouse models indicate the functional importance of CFTR in intestinal and pancreatic fluid transport, as well as in male fertility (Grubb et al., 1999, *Physiol. Rev.* 79:S193-S214; Wong, P. Y., 1997, *Mol. Hum. Reprod.* 4:107-110). However, the mechanisms remain unclear by which defective CFTR produces airway disease, which is the principal cause of morbidity and mortality in CF (Pilewski et al., 1999, *Physiol. Rev.* 79:S215-S255). Major difficulties in understanding airway disease in CF include the inadequacy of CF mouse models, which manifest little or no airway disease, the lack of large animal models of CF, and the limited availability of human CF airways that have not been damaged by chronic infection and inflammation. High-affinity, CFTR-selective inhibitors have not been available to study airway disease mechanisms in CF or to create the CF phenotype in large animal models.

High-affinity CFTR inhibitors also have clinical applications in the therapy of secretory diarrheas and cystic kidney disease, and in inhibiting male fertility. The compounds diphenylamine-2-carboxylate (DPC) and 5-nitro-2-(3-phenylpropyl-amino)benzoate (NPPB) inhibit CFTR at high concentrations but are non-specific in their inhibitory action (Cabantchik et al., 1992, *Am. J. Physiol.* 262:C803-C827; McDonough et al., 1994, *Neuron* 13:623-634; Schultz et al., 1999, *Physiol. Rev.* 79:S109-S144). The best CFTR inhibitor available for electrophysiological and other cell-based studies, glibenclamide, is used at concentrations of >100 μM (Sheppard et al., 1992, *J. Gen. Physiol.* 100:573-591; Hongre et al, 1994, *Pflugers Arch.* 426:284-287). However, at this concentration glibenclamide also inhibits other Cl$^-$ transporters as well as K$^+$ channels (Edwards et al., 1993, *Br. J. Pharmacol.* 110:1280-1281; Rabe et al., 1995, *Pflugers Arch.* 429:659-662; Yamazaki et al., 1997, *Circ. Res.* 81:101-109). Effective small molecule inhibitors of other ion transport proteins are known, but no small molecules with specific CFTR inhibitory ability suitable for therapy of secretory diseases have been available.

There is accordingly a need for CFTR inhibitor compounds and methods of using such compounds for development of animal models useful in the study and treatment of CF and the treatment and control of secretory disorders. The present invention addresses these needs, as well as others, and overcomes deficiencies found in the background art.

SUMMARY OF THE INVENTION

The invention provides compositions, pharmaceutical preparations and methods for inhibition of cystic fibrosis transmembrane conductance regulator protein (CFTR) that are useful for the study and treatment of CFTR-mediated diseases and conditions. The compositions and pharmaceutical preparations of the invention may comprise one or more thiazolidinone compounds or derivatives, and may additionally comprise one or more pharmaceutically acceptable carriers, excipients and/or adjuvants. The methods of the invention comprise, in certain embodiments, administering to a patient suffering from a CFTR-mediated disease or condition, an efficacious amount of a thiazolidinone compound or derivative. In other embodiments the invention provides methods of inhibiting CFTR that comprise contacting cells in a subject with an effective amount of a thiazolidinone compound or derivative. In addition, the invention features a non-human animal model of CFTR-mediated disease which model is produced by administration of a thiazolidinone compound or derivative to a non-human animal in an amount sufficient to inhibit CFTR.

These and other objects and advantages of the invention will be apparent from the detailed description below.

BRIEF DESCRIPTION OF THE DRAWINGS

The invention will be more fully understood by reference to the following drawings, which are for illustrative purposes only.

FIG. 3D is a graphical representation of whole-cell patch clamp of CFTR-expressing FRT cells showing membrane currents elicited at +80 mV (open circles) and −100 mV (closed circles). CFTR was stimulated by 5 µM forskolin followed by addition of 2 µM $CFTR_{inh}$-172.

FIG. 3E is a graphic illustration showing that alternate stimulation was interrupted (a-c) to apply graded membrane potentials.

FIG. 3F is a graphical representation of current-voltage relationships under basal conditions (control, open circles), after forskolin stimulation (filled circles), and following addition of 0.2 µM $CFTR_{inh}$-172 giving ~50% inhibition (open triangles).

Figure 1A:
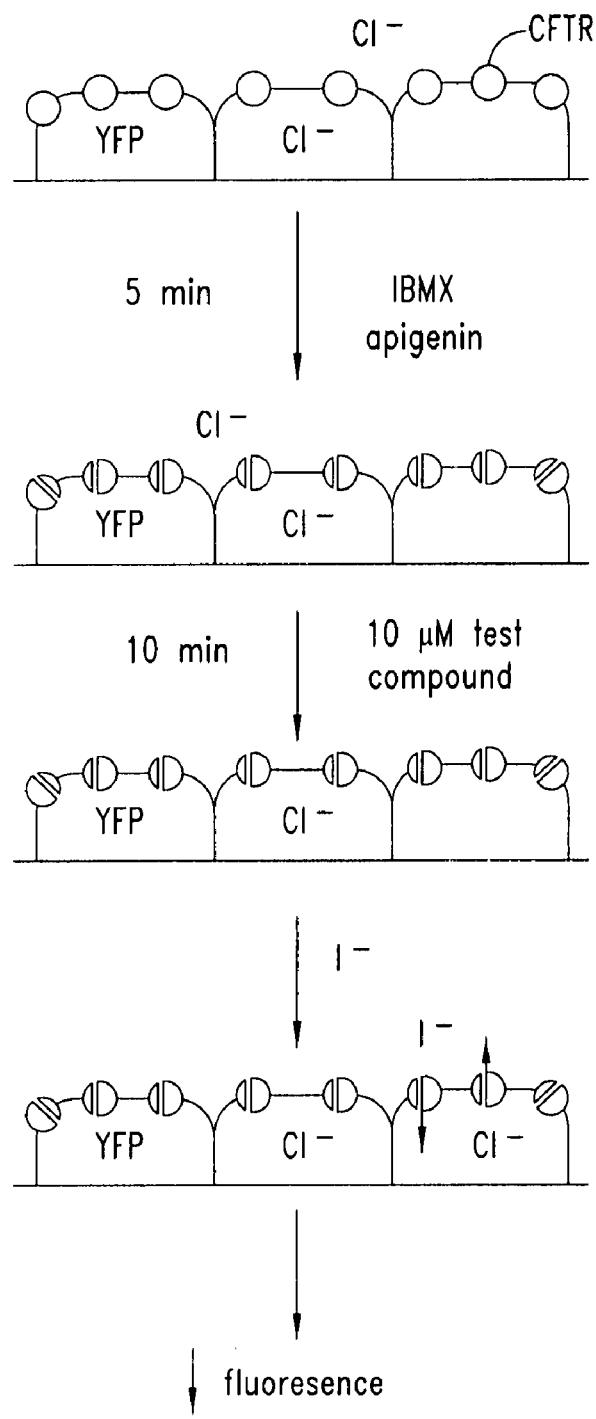
FIG. 1A is a schematic representation of a screening technique used for detection of CFTR inhibitors. CFTR was maximally stimulated by multiple agonists in stably transfected epithelial cells co-expressing human CFTR and a yellow fluorescent protein (YFP) having Cl$^-$/I$^-$ sensitive fluorescence. After addition of a test compound, I$^-$ influx was induced by adding an I$^-$ containing solution.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It should be noted that, as used herein and in the appended claims, the singular forms "a", "an", and "the" include plural referents unless the context clearly dictates otherwise. Thus, for example, reference to "an inhibitor" includes a plurality of such inhibitors, and reference to "the cell" includes reference to one or more cells and equivalents thereof known to those skilled in the art, and so forth.

The publications discussed herein are provided solely for their disclosure prior to the filing date of the present application, and are incorporated herein by reference. Nothing herein is to be construed as an admission that the present invention is not entitled to antedate such publication by virtue of prior invention. Further, the dates of publication provided may be different from the actual publication dates that may need to be independently confirmed.

The definitions used herein are provided for reason of clarity, and should not be considered as limiting. The technical and scientific terms used herein are intended to have the same meaning as commonly understood by those of ordinary skill in the art to which the invention pertains.

DETAILED DESCRIPTION OF THE INVENTION

The invention is based on the discovery of thiazolidinone compounds and derivatives that are high-affinity CFTR inhibitors. The structure of the compounds and derivatives of the invention, as well as pharmaceutical formulations and methods of use are described in more detail below.

DEFINITIONS

A "cystic fibrosis transmembrane conductance regulator protein-mediated condition or symptom" or "CFTR-mediated condition or symptom" means any condition, disorder or disease, or symptom of such condition, disorder, or disease, that results from activity of cystic fibrosis transmembrane conductance regulator protein (CFTR), e.g., activity of CFTR in ion transport. Such conditions, disorders, diseases, or symptoms thereof are treatable by inhibition of CFTR activity, e.g., inhibition of CFTR ion transport. CFTR activity has been implicated in, for example, intestinal secretion in response to various agonists, including cholera toxin (see, e.g., Snyder et al. 1982 *Bull. World Health Organ.* 60:605-613; Chao et al. 1994 *EMBO J.* 13:1065-1072; Kimberg et al. 1971 *J. Clin. Invest.* 50:1218-1230).

A "CFTR inhibitor" as used herein is a compound that reduces the efficiency of ion transport by CFTR, particularly with respect to transport of chloride ions by CFTR. Preferably CFTR inhibitors of the invention are specific CFTR inhibitors, i.e., compounds that inhibit CFTR activity without significantly or adversely affecting activity of other ion transporters, e.g., other chloride transporters, potassium transporters, and the like. Preferably the CFTR inhibitors are high-affinity CFTR inhibitors, e.g., have an affinity for CFTR of at least about one micromolar, usually about one to five micromolar.

"Treating" or "treatment" as used herein covers the treatment of a disease, condition, disorder or symptom in a subject, wherein the disease, condition, disorder or symptom is mediated by the activity of CFTR, and includes: (1) preventing the disease, condition, or disorder, i.e. causing the clinical symptoms of the disease not to develop in a subject that may be exposed to or predisposed to the disease, condition, or disorder, but does not yet experience or display symptoms thereof, (2) inhibiting the disease, condition or disorder, i.e., arresting or reducing the development of the disease, condition or disorder, or its clinical symptoms, or (3) relieving the disease, condition or disorder, i.e., causing regression of the disease, condition or disorder, or its clinical symptoms.

A "therapeutically effective amount" or "efficacious amount" means the amount of a compound of the invention that, when administered to a mammal or other subject in need thereof, is sufficient to effect treatment, as defined above, for diseases, conditions, disorders or symptoms mediated by the activity of CFTR. The amount of a compound of the invention that constitutes a "therapeutically effective amount" will vary depending on the compound, the disease and its severity and the age, weight, etc., of the subject to be treated, but can be determined routinely by one of ordinary skill in the art having regard to his own knowledge and to this disclosure.

The terms "subject" and "patient" mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound of the invention means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula C=C(OR) where R is hydrogen, alkyl, alkenyl, alkynyl, aryl, heteroaryl, aralkyl, heteroaralkyl, cycloalkyl or heterocyclyl.

A "pharmaceutically acceptable enol ester" of a compound of the invention means an enol ester that is pharmaceutically acceptable and that possesses the desired pharmacological activity of the parent compound, and includes, but is not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

A "pro-drug" means any compound that releases an active parent compound of formula (I) in vivo when the prodrug is administered to a mammalian subject. Prodrugs of the compounds of formula (I) contain functional groups that, under standard physiological conditions, are hydrolyzed into the corresponding carboxy, hydroxy, amino or sulfhydryl group. Examples of such functional groups include, but are not limited to, esters (e.g., acetate, formate and benzoate derivatives) and carbamates (e.g., N,N-dimethylaminocarbonyl) of hydroxy groups in compounds of formula (I), and the like. Additional examples include dipeptide or tripeptide esters of hydroxy or carboxy groups in compounds of formula (I), and the like. The preparation of such functional groups is well known in the art. For example, a compound of formula (I) having a hydroxy group attached thereto (e.g., when $X_1$, $X_2$, $X_3$, $Y_1$, $Y_2$ or $Y_3$ is hydroxy) may be treated with a carboxylic acid or a dipeptide having a free carboxy terminus under esterification conditions well known in the art to yield the desired ester functional group. Likewise, a compound of formula (I) having a free carboxy group attached thereto may be treated with an alcohol or a tripeptide containing a hydroxy group such as a serine residue (e.g., —N(H)—C(H)(CH$_2$OH)—C(O)—) under esterification conditions well known in the art to produce the desired ester functional group. In addition, compounds of formula (I) having a carboxylic ester group attached thereto may be treated with a different carboxylic ester under standard transesterification conditions to produce compounds of formula (I) with the desired functional ester group attached thereto. All such functional groups are considered to be within the scope of this invention.

The term "organic group" and "organic radical" as used herein means any carbon-containing group, including hydrocarbon groups that are classified as an aliphatic group, cyclic group, aromatic group, functionalized derivatives thereof and/or various combination thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, n-octyl, dodecyl, octadecyl, amyl, 2-ethylhexyl, and the like. Suitable substituents include carboxy, protected carboxy, amino, protected amino, halo, hydroxy, protected hydroxy, mercapto, lower alkylthio, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triflorom- ethyl, mono-substituted amino, di-substituted amino, lower alkoxy, mercapto, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, mercapto, alkylthio, alkylsulfonyl, halo, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo group" or "halogen" are used interchangeably herein and refer to the fluoro, chloro, bromo or iodo groups. Preferred halogens are chloro and fluoro.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans-decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, mercapto, alkylthio, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl) amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2-, 3- or 4-chlorophenyl, 2,6-dichlorophenyl, 2,5-dichlorophenyl, 3,4-dichlorophenyl, 2-, 3- or 4-bromophenyl, 3,4-dibromophenyl, 3-chloro-4-fluorophenyl, 2-, 3- or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2-, 3- or 4-nitrophenyl; a cyanophenyl group, for example, 2-, 3- or 4-cyanophenyl; a mono- or di(alkyl)phenyl group such as 2-, 3- or 4-methylphenyl, 2,4-dimethylphenyl, 2-, 3- or 4-(iso-propyl)phenyl, 2-, 3- or 4-ethylphenyl, 2-, 3- or 4-(n-propyl)phenyl and the like; a mono or di(alkoxy) phenyl group, for example, 2,6-dimethoxyphenyl, 2-, 3- or 4-(isopropoxy)phenyl, 2-, 3- or 4-(t-butoxy)phenyl, 3-ethoxy-4-methoxyphenyl and the like; 2-, 3- or 4-trifluoromethylphenyl; a mono- or dicarboxyphenyl or (protected carboxy)phenyl group such as 2-, 3- or 4-carboxyphenyl or 2,4-di(protected carboxy)phenyl; a mono- or di(hydroxymethyl)phenyl or (protected hydroxymethyl)phenyl such as 2-, 3- or 4-(protected hydroxymethyl)phenyl or 3,4-di(hydroxymethyl)phenyl; a mono- or di(aminomethyl)phenyl or (protected aminomethyl)phenyl such as 2-, 3- or 4-(aminomethyl)phenyl or 2,4-(protected aminomethyl)phenyl; or a mono- or di(N-(methylsulfonylamino))phenyl such as 2-, 3- or 4-(N-(methylsulfonylamino)))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples include such groups as 2-phenyl-1-chloroethyl, 2-(4'-methoxyphenyl)ethyl, 4-(2',6'-dihydroxy phenyl)-n-hexyl, 2-(5'-cyano-3'-methoxyphenyl)-n-pentyl, 3-(2',6'-dimethylphenyl)propyl, 4-chloro-3-aminobenzyl, 6-(4'-methoxyphenyl)-3-carboxyhexyl, 5-(4'-aminomethylphenyl)-3-(aminomethyl)pentyl, 5-phenyl-3-oxopent-1-yl, (4-hydroxynapth-2-yl)methyl and the like.

As noted above, the term "aromatic" or "aryl" refers to five and six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms. These five-membered or six-membered rings may be fully unsaturated.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, mercapto, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature or element may, but need not, occur, and that the description includes instances where the event or circumstance occurs and instances in which it does not. For example, "heterocyclo group optionally mono- or disubstituted with an alkyl group" means that the alkyl may, but need not, be present, and the description includes situations where the heterocyclo group is mono- or disubstituted with an alkyl group and situations where the heterocyclo group is not substituted with the alkyl group.

The term "electron-withdrawing group" refers to the ability of a functional group on a molecule to draw electrons to itself more than a hydrogen atom would if the hydrogen atom occupied the same position in the molecule. Examples of electron-withdrawing groups include, but are not limited to, halogen groups, —C(O)R groups (where R is alkyl); carboxylic acid and ester groups; —$NR_3^+$ groups (where R is alkyl or hydrogen); azo; nitro; —OR and —SR groups (where R is hydrogen or alkyl); and organic groups (as defined herein) containing such electron-withdrawing groups, such as haloalkyl groups (including perhaloalkyl groups), and the like.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either an individual enantiomer or as a mixture of thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Overview

The invention provides thiazolidinone compositions, thiazolidinone derivatives compositions and methods of their use in high affinity inhibition of cystic fibrosis transmembrane conductance regulator protein (CFTR) and for the study and treatment of CFTR-mediated diseases and conditions. The discovery of the subject thiazolidinone compounds and derivatives was based on screening of numerous potential candidate compounds using an assay designed to identify CFTR inhibitors that interact directly with CFTR. Without being held to any particular theory or mode of operation, since multiple CFTR activators that work on different activating pathways were included in the studies leading to identification of the subject compounds, the inhibitory compounds of the invention likely effect inhibition by acting at or near the CFTR Cl⁻ transporting pathway. A screening of 50,000 diverse compounds identified several 2-thioxo-4-thiazolidinone compounds and derivatives as effective CFTR inhibitors. These compounds and derivatives are unrelated chemically and structurally to previously known CFTR activators or to the previously known CFTR inhibitors DPC, NPPB or glibenclamide. The most potent CFTR inhibitor identified from screening had a $K_I$ of ~300 nM for inhibition of Cl⁻ current in human airway cells. Inhibition was rapid, reversible and CFTR-specific.

The compositions and methods of the invention will now be described in more detail.

Thiazolidinone Compounds and Derivatives

The thiazolidinone compounds and derivatives used in the compositions and methods of the invention comprise a heterocyclic ring of five or more atoms, including an aryl substituted nitrogen, at least one sulfur, oxygen or selenium heteroatom, and one or more carbonyl or thiocarbonyl groups associated with the heterocyclic ring. More specifically, the subject thiazolidinone compounds and derivatives may have the following formula (I):

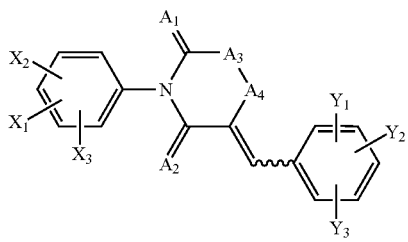

(I)

wherein $X_1$, $X_2$ and $X_3$ are independently chosen from hydrogen, an organic group, a halo group, a nitro group, an azo group, a hydroxyl group and a mercapto group; $Y_1$, $Y_2$ and $Y_3$ are independently chosen from hydrogen, an organic group, a halo group, a nitro group, an azo group, a hydroxyl group and a mercapto group; $A_1$ and $A_2$ are independently chosen from oxygen and sulfur, $A_3$ is chosen from sulfur and selenium; and $A_4$ comprises one or more carbons or heteroatoms and may be present or absent; or a pharmaceutically acceptable derivative thereof, as an individual stereoisomer or a mixture thereof. Where $A_4$ is absent the central heterocyclic ring is a five membered ring.

In certain embodiments, the thiazolidinone compounds and derivatives of formula (I) above comprise the formula (Ia):

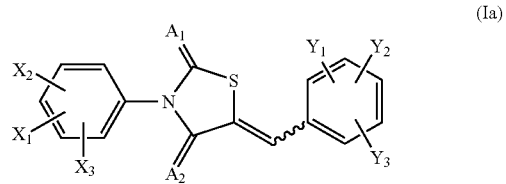

(Ia)

wherein $X_1$, $X_2$ and $X_3$ are independently chosen from hydrogen, an organic group, a halo group, a nitro group, an azo group, a hydroxyl group and a mercapto group; $Y_1$, $Y_2$ and $Y_3$ are independently chosen from hydrogen, an organic group, a halo group, a nitro group, an azo group, a hydroxyl group and a mercapto group; and $A_1$ and $A_2$ are independently chosen from oxygen and sulfur. In specific embodiments, $X_1$ may be an electron withdrawing group, and may comprise a haloalkyl group, dihaloalkyl group, trihaloalkyl group (e.g., trifluoroalkyl group) or a fluoro group. $Y_2$ is independently chosen from the group consisting of alkyl, hydroxyl, carboxyl, nitro, carbonate, carbamate, alkoxy, alkylcarbonyl, and halo groups, $Y_1$ is independently chosen from hydroxyl and bromo groups, and $Y_3$ is independently chosen from hydrogen and a nitro group.

The subject thiazolidinone compounds and derivatives of formula (I) in many embodiments may comprise 3-aryl-5-arylmethylene-2-thioxo-4-thiazolidinones of the formula (Ib)

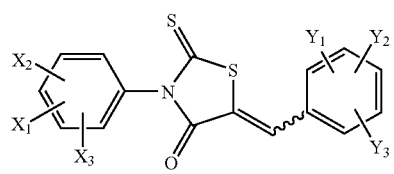

(Ib)

wherein at least one of $X_1$, $X_2$ and $X_3$ is an electron-withdrawing group; and $Y_1$, $Y_2$ and $Y_3$ are independently chosen from hydrogen, alkyl, hydroxyl, carboxyl, nitro, carbonate, carbamate, alkoxy, alkylcarbonyl, and a halo group. In one embodiment $X_1$ is at a position selected from 2, 3, or 4; $Y_2$ is at a position selected from 2, 3, or 4; and $Y_1$ and $Y_3$ may be hydrogen.

The 3-aryl-5-arylmethylene-2-thioxo-4-thiazolidinones may more specifically have the formula (Ic):

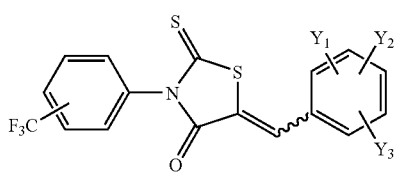

(Ic)

wherein $Y_1$-$Y_3$ are as described above. In one embodiment the trifluoromethyl group is at a position selected from 2, 3, or 4; $Y_2$ is at a position selected from 2, 3, or 4; where $Y_1$ and $Y_3$ may be hydrogen in this embodiment.

In some embodiments of the invention, the thiazolidinone compounds of the invention may comprise:

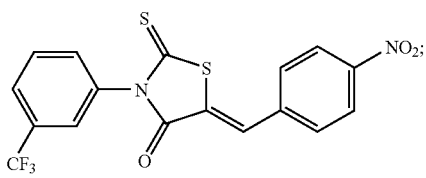

i.e., 3-[(3-trifluoromethyl)phenyl]-5-[(4-nitrophenyl)methylene]-2-thioxo-4-thiazolidinone;

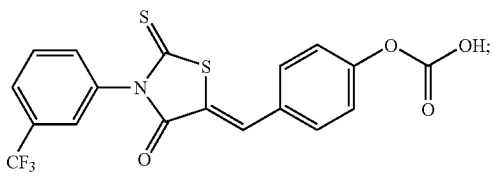

i.e., 3-[(3-trifluoromethyl)phenyl]-5-[(4-oxycarboxyphenyl)methylene]-2-thioxo-4-thiazolidinone;

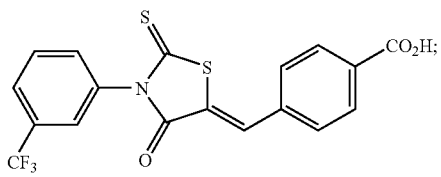

i.e., 3-[(3-trifluoromethyl)phenyl]-5-[(4-carboxyphenyl)methylene]-2-thioxo-4-thiazolidinone;

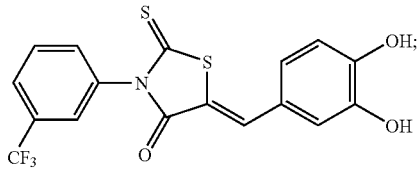

i.e., 3-[(3-trifluoromethyl)phenyl]-5-[(3,4-dihydroxyphenyl)methylene]-2-thioxo-4-thiazolidinone;

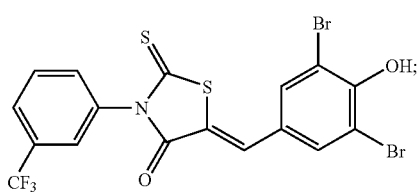

i.e., 3-[(3-trifluoromethyl)phenyl]-5-[(3,5-dibromo-4-hydroxyphenyl)methylene]-2-thioxo-4-thiazolidinone; and

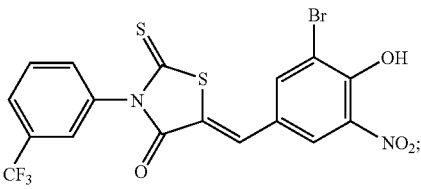

i.e., 3-[(3-trifluoromethyl)phenyl]-5-[(3-bromo-4-hydroxy-5-nitrophenyl)methylene]-2-thioxo-4-thiazolidinone. Alternatively, the trifluoromethyl group in any of the above recited compounds may be position 2 or position 4 of the phenyl ring.

Pharmaceutical Preparations

Also provided by the invention are pharmaceutical preparations of the subject thiazolidinone compounds described above. The subject compounds can be incorporated into a variety of formulations for therapeutic administration by a variety of routes. More particularly, the compounds of the present invention can be formulated into pharmaceutical compositions by combination with appropriate, pharmaceutically acceptable carriers, diluents, excipients and/or adjuvants, and may be formulated into preparations in solid, semi-solid, liquid or gaseous forms, such as tablets, capsules, powders, granules, ointments, solutions, suppositories, injections, inhalants and aerosols. Preferably, the formulations are free of detectable DMSO (dimethyl sulfoxide), which is not a pharmaceutically acceptable carrier, diluent, excipient, or adjuvant for non-topical, parenteral administration or enteral administration. The formulations may be designed for administration to subjects or patients in need thereof via a number of different routes, including oral, buccal, rectal, parenteral, intraperitoneal, intradermal, transdermal, intracheal, etc., administration.

In one embodiment, topical administration (e.g., by transdermal administration) is of interest. Topical formulations can be in the form of a transdermal patch, ointment, paste, lotion, cream, gel, and the like. Topical formulations may include one or more of a penetrating agent, thickener, diluent, emulsifier, dispersing aid, or binder. Where the compound is formulated for transdermal delivery, the compound may be formulated with or for use with a penetration enhancer. Penetration enhancers, which include chemical penetration enhancers and physical penetration enhancers, facilitate delivery of the compound through the skin, and may also be referred to as "permeation enhancers" interchangeably. Physical penetration enhancers include, for example, electrophoretic techniques such as iontophoresis, use of ultrasound (or "phonophoresis"), and the like. Chemical penetration enhancers are agents administered either prior to, with, or immediately following compound administration, which increase the permeability of the skin, particularly the stratum corneum, to provide for enhanced penetration of the drug through the skin.

Compounds that have been used to enhance skin permeability include: the sulfoxides dimethylsulfoxide (DMSO) and decylmethylsulfoxide ($C_{10}$ MSO); ethers such as diethylene glycol monoethyl ether, dekaoxyethylene-oleylether, and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; the 1-substituted azacycloheptan-2-ones, particularly 1-n-dodecylcyclazacycloheptan-2-one; alcohols such as ethanol, propanol, octanol, benzyl alcohol, and the like; petrolatums, such as petroleum jelly (petrolatum), mineral oil (liquid petrolatum), and the like; fatty acids such as $C_8$-$C_{22}$ and other fatty acids (e.g., isostearic acid, octanoic acid, oleic acid, lauric acid, valeric acid); $C_8$-$C_{22}$ fatty alcohols (e.g., oleyl alcohol, lauryl alcohol); lower alkyl esters of $C_8$-$C_{22}$ fatty acids and other fatty acids (e.g., ethyl oleate, isopropyl myristate, butyl stearate, methyl laurate, isopropyl myristate, isopropyl palmitate, methylpropionate, ethyl oleate); monoglycerides of $C_8$-$C_{22}$ fatty acids (e.g., glyceryl monolaurate); tetrahydrofurfuryl alcohol polyethylene glycol ether; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; di-lower alkyl esters of $C_6$-$C_8$ diacids (e.g., diisopropyl adipate); ethyl acetate; acetoacetic ester; polyols and esters thereof such as propylene glycol, ethylene glycol, glycerol, butanediol, polyethylene glycol, and polyethylene glycol monolaurate; amides and other nitrogenous compounds such as urea, dimethylacetamide (DMA), dimethylformamide (DMF), 2-pyrrolidone, N-alkylpyrrolidone, e.g., 1-methyl-2-pyrrolidone; ethanol amine, diethanol amine and triethanolamine; terpenes; alkanones, and organic acids, particularly salicylic acid and salicylates, citric acid and succinic acid. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneruas et al., J Pharm Pharmacol 2002; 54(4):499-508; Karande et al., Pharm Res 2002; 19(5):655-60; Vaddi et al., J Pharm Sci 2002 July; 91(7):1639-51; Ventura et al., J Drug Target 2001; 9(5):379-93; Shokri et al., Int J Pharm 2001; 228(1-2):99-107; Suzuki et al., Biol Pharm Bull 2001; 24(6):698-700; Alberti et al., J Control Release 2001; 71(3):319-27; Goldstein et al., Urology 2001; 57(2):301-5; Kiijavainen et al., Eur J Pharm Sci 2000; 10(2):97-102; and Tenjarla et al., Int J Pharm 1999; 192(2):147-58.

Where the compound is formulated with a chemical penetration enhancer, the penetration enhancer is selected for compatibility with the compound, and is present in an amount sufficient to facilitate delivery of the compound through skin of a subject, e.g., for delivery of the compound to the systemic circulation. In one embodiment, the compound is formulated with a penetration enhancer other than DMSO.

In one embodiment, the compound is provided in a drug delivery patch, e.g., a transmucosal or transdermal patch, and can be formulated with a penetration enhancer. The patch generally includes a backing layer, which is impermeable to the compound and other formulation components, a matrix in contact with one side of the backing layer, which matrix provides for sustained release, which may be controlled release, of the compound, and an adhesive layer, which is on the same side of the backing layer as the matrix. The matrix can be selected as is suitable for the route of administration, and can be, for example, and can be a polymeric or hydrogel matrix.

In pharmaceutical dosage forms, the subject compounds of the invention may be administered in the form of their pharmaceutically acceptable derivative, such as a salt, or they may also be used alone or in appropriate association, as well as in combination, with other pharmaceutically active compounds. The following methods and excipients are merely exemplary and are in no way limiting.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Of particular interest is formulation of the subject thiazolidinone compounds with a buffering agent, to provide for protection of the compound from low pH of the gastric environment. It may also be preferable to provide an enteric coating so as to avoid precipitation of the compound while in transit through the stomach.

The subject compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Solubilizers of particular interest include vitamin E TPGS (d-α-tocopheryl polyethylene glycol 1000 succinate), cyclodextrins, and the like.

The compounds of the invention can be utilized in aerosol formulation to be administered via inhalation. The compounds of the present invention can be formulated into pressurized acceptable propellants such as dichlorodifluoromethane, propane, nitrogen and the like.

Furthermore, the subject compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

Depending on the subject and condition being treated and on the administration route, the subject compounds may be administered in dosages of, for example, 0.1 μg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. The inventors have found that cholera toxin-induced intestinal fluid secretion in mice is effectively blocked by a single intraperitoneal dose of about 10-20 micrograms with a dosage of about ten times greater being effective in rats. Thus, for example, oral dosages may be about ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

For use in the subject methods, the subject compounds may be formulated with other pharmaceutically active agents, including other CFTR-inhibiting agents.

Pharmaceutically acceptable excipients usable with the invention, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Kits with unit doses of the subject compounds, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Conditions Amenable to Treatment Using the CFTR Inhibitors of the Invention

The CFTR inhibitors disclosed herein are useful in the treatment of a CFTR-mediated condition, i.e., any condition, disorder or disease, or symptom of such condition, disorder, or disease, that results from activity of CFTR, e.g., activity of CFTR in ion transport. Such conditions, disorders, diseases, or symptoms thereof are amenable to treatment by inhibition of CFTR activity, e.g., inhibition of CFTR ion transport.

In one embodiment, the CFTR inhibitors of the invention are used in the treatment of conditions associated with aberrantly increased intestinal secretion, particularly acute aberrantly increased intestinal secretion. CFTR activity has been implicated in intestinal secretion in response to various agonists, including cholera toxin (see, e.g., Snyder et al. 1982 *Bull. World Health Organ.* 60:605-613; Chao et al 1994 *EMBO J.* 13:1065-1072; Kimberg et al. 1971 *J. Clin. Invest.* 50:1218-1230). Thus CFTR inhibitors of the invention can be administered in an amount effective to inhibit CFTR ion transport and thus decrease intestinal fluid secretion.

Thus, CFTR inhibitors can be used in the treatment of intestinal inflammatory disorders and diarrhea, particularly secretory diarrhea. Secretory diarrhea is the biggest cause of infant death in developing countries, with about 5 million deaths annually (Gabriel et al., 1994 *Science* 266: 107-109). Several studies, including those using CF mice, indicate that CFTR is the final common pathway for intestinal chloride ion (and thus fluid) secretion in response to various agonists (Snyder et al., 1982, *Bull. World Health Organ.* 60: 605-613; Chao et al., 1994 *EMBO. J.* 13: 1065-1072; and Kimberg et al., 1971, *J. Clin. Invest.* 50: 1218-1230). The mouse models of intestinal fluid secretion used herein indicate that CFTR inhibition by systemic administration of the inhibitor at a non-toxic dose effectively blocked intestinal fluid secretion induced by cholera toxin (see Examples).

Diarrhea that may be amenable to treatment using the CFTR inhibitors of the invention can result from exposure to a variety of pathogens or agents including, without limitation, cholera toxin (*Vibrio cholera*), *E. coli* (particularly enterotoxigenic (ETEC)), *Shigella, Salmonella, Campylobacter, Clostridium difficile*, parasites (e.g., *Giardia, Entamoeba histolytica, Cryptosporidiosis, Cyclospora*), diarrheal viruses (e.g., rotavirus), food poisoning, or toxin exposure that results in increased intestinal secretion mediated by CFTR.

Other diarrheas include diarrhea associated with AIDS (e.g., AIDS-related diarrhea), and inflammatory gastrointestinal disorders, such as ulcerative colitis, inflammatory bowel disease (IBD), Crohn's disease, and the like. It has been reported that intestinal inflammation modulates the expression of three major mediators of intestinal salt transport and may contribute to diarrhea in ulcerative colitis both by increasing transepithelial Cl⁻ secretion and by inhibiting the epithelial NaCl absorption (see, e.g., Lohi et al., 2002, *Am. J. Physiol. Gastrointest. Liver Physiol.* 283(3):G567-75).

CFTR inhibitors of the invention can also be used in treatment of conditions such as polycystic kidney disease, and find further use as male infertility drugs, by inhibition of CFTR activity in the testis.

CFTR inhibitors of the invention can be further screened in larger animal models (e.g., the rabbit model described in Spira et al., 1981, *Infect. Immun.* 32:739-747). In addition, analysis of stool output using live *Vibrio cholerae* can also be examined to further characterize the CFTR inhibitors of the invention.

Non-Human Animal Models and Human Tissue Models of CFTR-Deficiencies

The CFTR inhibitors of the invention can also be used to generate non-human animal models of disease, where the disease is associated with decreased CFTR function (e.g., decreased ion transport). There is increasing evidence that defective fluid and macromolecular secretion by airway submucosal glands leads to impaired mucociliary and bacterial clearance in CFTR-deficient subjects, particularly in those affected with cystic fibrosis (CF); however, functional studies in human airway glands have been restricted to severely diseased airways obtained at the time of lung transplantation (Jayaraman et al. 2001 *Proc. Natl. Acad. Sci. USA* 98:8119-8123). Acute CFTR inhibition permits determination of the role of CFTR in water, salt and macromolecule secretion by submucosal glands. High-affinity CFTR inhibitors permit the pharmacological creation of non-human animal models that mimic CFTR-deficiency in humans, e.g., mimics the human CF phenotype. In particular, large animal models of CFTR deficiency (e.g., CF) find particular use in elucidating the pathophysiology of initiation and progression of airway disease in CF, and in evaluating the efficacy of CF therapies, e.g., screening candidate agents for treatment of CFTR-deficiencies or symptoms thereof.

Inhibition of CFTR ion transport can be manifested in airway and pancreatic disorders, as well as infertility in males. For example, inhibition of CFTR channels in the lungs and airways influences airway surface fluids leading to accumulation of mucus, which in turn plugs airways and collects heavily on the lung walls, providing a prime environment for infection to occur, which in turn can lead to chronic lung disease. This same phenomenon occurs in the pancreas, where the accumulated mucus disrupts the exocrine function of the pancreas and prevents essential food-processing enzymes from reaching the intestines.

Such non-human animal models can be generated by administration of an amount of a CFTR inhibitor effective to decrease CFTR activity in ion transport. Of particular interest is the use of the CFTR inhibitors of the invention to induce the cystic fibrosis (CF) phenotype in a non-human animal. Administration of an amount of a CFTR inhibitor effective to inhibit CFTR receptors in, for example, lung effectively mimics the CFTR defect found in CF. Routes of delivery for CFTR inhibitor are discussed in detail above. Depending on the non-human animal used, the subject compounds may be administered in dosages of, for example, 50 to 500 µg/kg body weight one to three times a day by an intraperitoneal, subcutaneous, or other route to generate the non-human animal models. Oral dosages may be up to about ten times the intraperitoneal or subcutaneous dose.

Non-human animal models of CFTR-associated disease can be used as models of any appropriate condition associated with decreased CFTR activity. Such conditions include those that are associated with CFTR mutations, which mutations result in abnormalities in epithelial ion and water transport. These abnormalities can in turn be associated with derangements in airway mucociliary clearance, as well as in other mucosal epithelia and ductal epithelia. Conditions that can be pharmacologically modeled by inducing a CFTR-deficient phenotype in a non-human animal include, without limitation, cystic fibrosis (including atypical CF), idiopathic chronic pancreatitis, vas deferens defects, mild pulmonary disease, asthma, and the like. For a review of disorders associated with impaired CFTR function, see, e.g., Noone et al. *Respir Res* 2 328-332 (2001). CFTR inhibitor-generated non-human animal models can also serve as models of microbial infection (e.g., bacterial, viral, or fungal infection, particularly respiratory infections) in a CFTR-deficient subject. In one embodiment of particular interest, the CFTR inhibitors of the invention are used to pharmacologically induce the cystic fibrosis (CF) phenotype.

Animals suitable for use in the production of the animal models of the invention include any animal, particularly a mammal, e.g., non-human primates (e.g., monkey, chimpanzee, gorilla, and the like), rodents (e.g., rats, mice, gerbils, hamsters, ferrets, and the like), lagomorphs, swine (e.g., pig, miniature pig), equine, canine, feline, and the like. Large animals are of particular interest.

The CFTR inhibitors can also be contacted with isolated human tissue to create ex vivo models of disease. Such tissue is contacted with an amount of a CFTR inhibitor effective to decrease CFTR activity in the tissue, which may be for as little as 15 minutes, or as much as two hours or more. Human tissues of interest include, without limitation, lung (including trachea and airways), liver, pancreas, testis, and the like. Physiological, biochemical, genomic or other studies can be carried out on the inhibitor-treated tissue to identify novel therapeutic target molecules that are important in the pathophysiology of a disease. For example, isolated tissue from humans without CF can be exposed to inhibitor sufficient to induce the CF phenotype and such studies can be carried out to identify novel therapeutic target molecules that are important in the pathophysiology of CF.

Synthesis of the Compounds of the Invention

Compounds of the invention may be prepared according to methods known to one skilled in the art, or by the methods similar to those disclosed in U.S. Pat. No. 5,326,770 and U.S. Pat. No. 6,380,186 (all of which are incorporated in full by reference herein), or by methods similar to the method described below.

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Theodora W. Greene, Peter G. M. Wuts, *Protective Groups in Organic Synthesis* (1999), 3rd Ed., Wiley-Interscience. The protecting group may also be a polymer resin such as a Wang resin or a 2-chlorotrityl chloride resin.

It will also be appreciated by those skilled in the art, although such protected derivatives of compounds of formula (I), as described above (e.g., in the Overview and in Thiazolidinone Compounds and Derivatives), may not possess pharmacological activity as such, they may be administered to a mammal and thereafter metabolized in the body to form compounds of the invention which are pharmacologically active. Such derivatives may therefore be described as "prodrugs". All prodrugs of compounds of formula (I) are included within the scope of the invention.

The following Reaction Schemes illustrate methods to make compounds of the invention. It is understood that one of ordinary skill in the art would be able to make the compounds of the invention by similar methods or by methods known to one skilled in the art. In general, starting components may be obtained from sources such as Aldrich, or synthesized according to sources known to those of ordinary skill in the art (see, e.g., Smith and March, *March's Advanced Organic Chemistry: Reactions, Mechanisms, and Structure,* 5th edition (Wiley Interscience, New York)). Moreover, the various substituted groups (e.g., $X_1$, $X_2$, $X_3$, $Y_1$, $Y_2$ and $Y_3$, etc.) of the compounds of the invention may be attached to the starting components, intermediate components, and/or final products according to methods known to those of ordinary skill in the art.

In the following Reaction Schemes, R represents an alkyl or aralkyl group and W represents a halogen atom, such as Cl, Br or I.

The following Reaction Scheme 1 is directed to the preparation of compounds of formula (1), which are compounds of the invention as described above (e.g., in the Overview and in Thiazolidinone Compounds and Derivatives), where $A_4$ is absent, and $A_1$, $A_2$, $A_3$, $X_1$, $X_2$, $X_3$, $Y_1$, $Y_2$, and $Y_3$ are as described above (e.g., in the Overview and in Thiazolidinone Compounds and Derivatives).

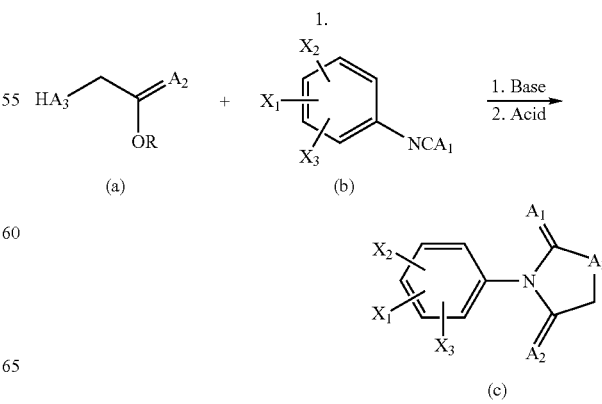

2.

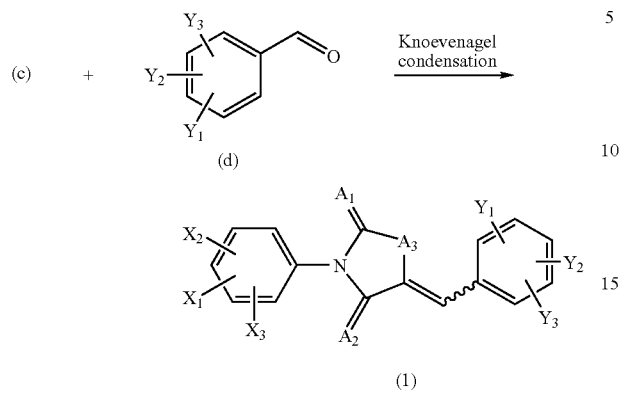

(1)

In general, compounds of formula (1) are prepared by first treating a compound of formula (a) with 1 equivalent of a base, such as NaOH, at ambient temperature. Compound of formula (b), dissolved in an appropriate solvent such as THF, is then added to the reaction mixture. The resulting reaction mixture is then stirred for a period of time of between about 1 hour to about 24 hours. An acid, such as HCl, is then added to the reaction mixture. The resulting reaction mixture is then stirred for a period of time of between about 1 hour to about 24 hours. The compound of formula (c) is then isolated from the reaction mixture by standard isolation and purification techniques. The compound of formula (c) is then treated with a compound of formula (d) under standard Knoevenagel condensation conditions to yield the desired product of formula (1).

Alternatively, compounds of formula (1) can be prepared according to the following Reaction Scheme 2 wherein $A_1$, $A_2$, $A_3$, $Y_1$, $Y_2$, and $Y_3$ are as described above (e.g., in the Overview and in Thiazolidinone Compounds and Derivatives), and W is halo:

REACTION SCHEME 2

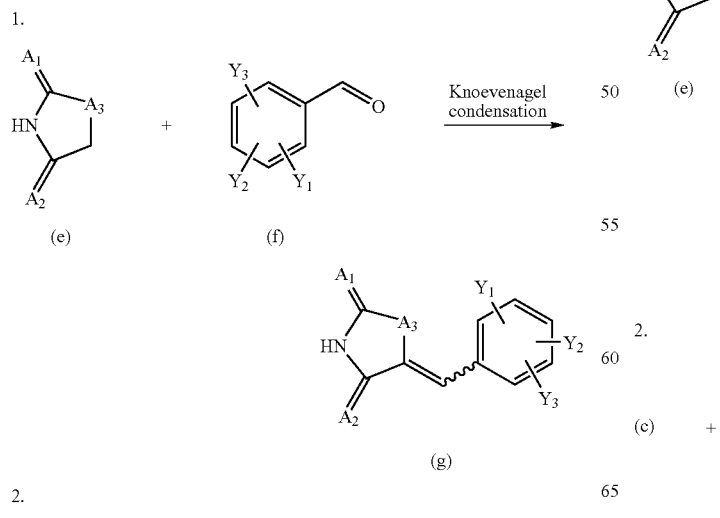

In general, the compounds of formula (1) can be prepared by first treating a compound of formula (e) with a compound of formula (f) under standard Knoevenagel condensation conditions, such as under reflux in the presence of catalytic amount of piperidine in glacial acetic acid, an alcohol or another appropriate solvent. The compound of formula (g) is then isolated from the reaction mixture by standard isolation and purification techniques. The compound of formula (g) is then treated with a compound of formula (h) under standard Ullmann condensation conditions, such as in the presence of Cu or $Cu_2O$ or CuO at elevated temperatures, to yield the desired product of formula (1).

Alternatively, compounds of formula (1) can be prepared according to the following Reaction Scheme 3 wherein $A_1$, $A_2$, $A_3$, $Y_1$, $Y_2$, and $Y_3$ are as described above (e.g., in the Overview and in Thiazolidinone Compounds and Derivatives) and W is halo.

REACTION SCHEME 3

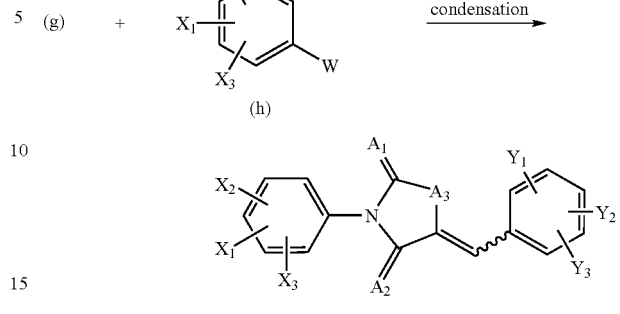

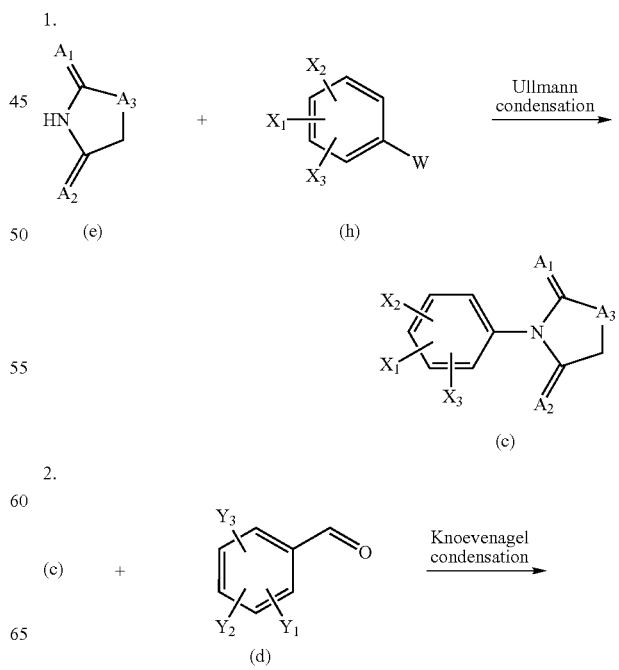

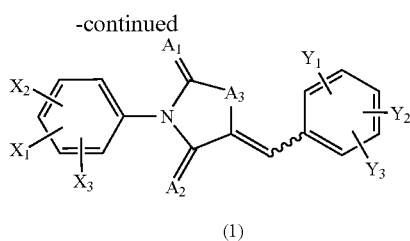

(1)

In this reaction scheme, the first step is the Ullmann condensation between the compound of formula (e) and the compound of formula (h) to produce the compound of formula (c), which then undergoes Knoevenagel condensation with a compound of formula (d) to yield the desired product of formula (1).

The starting compound of formula (e) can be purchased from different chemical suppliers or synthesized according to methods known to one skilled in the art, or by the methods similar to those disclosed in F. C. Brown et. al., *J. Am. Chem. Soc.,* 78, 384-388 (1956); R. E. Strube, *Organic Synthesis,* CV 4, 6; K. S. Markley and E. E. Reid, *J. Am. Chem. Soc.,* 52, 2137-2141 (all of which are incorporated in full by reference herein).

In a similar manner as described above, synthesis of 3-[(3-trifluoromethyl)phenyl]-5-[(4-carboxyphenyl)methylene]-2-thioxo-4-thiazolidinone (referred to herein as CFTR$_{inh}$-172) (see FIG. 1C) and analogs with different positions of the trifluoromethyl and carboxy substituents (see, e.g., FIG. 1D) was accomplished by Knoevenagel condensation of 2-thioxo-3-[a-trifluoromethyl-4-phenyl]-4-thiazolidinone (a=2, 3 or 4) with b-carboxybenzaldehyde (b=2, 3 or 4) in the presence of piperidine. The precipitate was filtered, washed with ethanol, dried and recrystallized 2-3 times from ethanol to give bright yellow crystals (70-85% yields). Structures were confirmed by $^1$H-NMR. Purity was >99% as judged by thin layer chromatography and HPLC.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The synthesis of compounds of the invention are exemplified with but not limited to the following examples.

Synthetic Example

Synthesis of 3-[(3-trifluoromethyl)phenyl]-5-[(4-carboxyphenyl)methylene]-2-thioxo-4-thiazolidinone A. To a stirred solution of 3-trifluoromethylaniline (1.6 g, 10 mmol) and triethylamine (1 g, 10 mmol) in ethyl acetate (10 mL) was added dropwise carbon disulfide (0.8 g, 10 mmol) during a 30-minute period. A mild exothermic reaction, which began when the addition was about half complete, was easily controlled by intermittent use of ice bath. After stirring overnight, the thick yellow slurry was filtered and the precipitate was washed with 50 mL of diethyl ether and air-dried to give 3 g (89%) of a pale yellow dithiocarbamate solid, m.p. 92-95° C. (dec.).

B. Sodium chloroacetate (prepared from chloroacetic acid (0.064 g, 0.46 mmol) in 0.6 mL of NaHCO$_3$ solution, pH 8-9) was stirred and cooled to 5-10° C. and the dithiocarbamate (0.3 g, 0.9 mmol) was added over a period of ten minutes. Stirring was continued while the flask was allowed to warm to ambient temperature. After 2 hours of stirring, the solution was cooled to 10° C. and acidified with concentrated hydrochloric acid and the reaction mixture was heated to 90-95° C. for 30 minutes. The resulting precipitate was filtered, washed with water and recrystallised from ethanol to give 0.103 g of 2-thioxo-3-(3-trifluoromethylphenyl)-4-thiazolidinone, as shiny crystals in 83% yield, m.p. 177-178° C., $^1$H NMR (300 MHz, CDCl$_3$): δ 4.18 (s, 2H, CH$_2$), 7.40 (d, 1H, phenyl, J=8.0 Hz), 7.48 (s, 1H, phenyl), 7.64 (t, 1H, phenyl, J=8.0 Hz), 7.72 (d, 1H, phenyl, J=7.6 Hz) ppm.

C. A mixture of 2-thioxo-3-(3-trifluoromethylphenyl)-4-thiazolidinone obtained above (0.1 g, 0.36 mmol) and 4-carboxybenzaldehyde (0.054 g, 0.36 mmol) in absolute alcohol (1 mL) and piperidine (1 drop) was stirred at reflux for 30 minutes. The yellow precipitate was filtered, washed with ethanol, dried and recrystallised from ethanol to yield 0.108 g (73%) of the title compound as yellow crystalline solid, m.p.: 180-182° C., $^1$H NMR (300 MHz, DMSO-d$_6$): δ 7.78 (d, 2H, carboxyphenyl, J=8.2 Hz), 7.80-8.00 (m, 5H, trifluoromethylphenyl and CH), 8.07 (d, 2H, carboxyphenyl, J=8.31 Hz), 13.20 (s, 1H, COOH, D$_2$O exchangeable) ppm.

D. In a similar manner as described above, the following compounds were prepared:

3-[(3-trifluoromethyl)phenyl]-5-[(3-carboxy-4-hydroxyphenyl)methylene]-2-thioxo-4-thiazolidinone;

3-[(3-trifluoromethyl)phenyl]-5-[(3,4,5-trihydroxyphenyl)methylene]-2-thioxo-4-thiazolidinone;

3-[(3-trifluoromethyl)phenyl]-5-[(2,3,4-trihydroxyphenyl)methylene]-2-thioxo-4-thiazolidinone;

3-[(3-trifluoromethyl-4-fluoro)phenyl]-5-[(3-carboxy-4-hydroxyphenyl)methylene]-2-thioxo-4-thiazolidinone; and 3-[(4-fluoro-3-trifluoromethyl)phenyl]-5-[(4-carboxyphenyl)methylene]-2-thioxo-4-thiazolidinone.

The following materials and methods were used in the examples that follow.

Cell Lines, Mice and Compounds

Fischer rat thyroid (FRT) cells coexpressing human wild-type CFTR and the halide indicator YFP-H148Q were generated as described previously (Galietta et al. 2001 *J. Biol. Chem.* 276:19723-19728). Cells were plated in 96-well black-walled microplates (Corning Costar) at a density of 20,000 cells per well in Coon's modified F12 medium supplemented with 5% fetal calf serum, 2 mM L-glutamine, 100 U/mL penicillin, and 100 μg/mL streptomycin. Assays were done at 48 hours after plating at which time cells were just confluent (~40,000 cells per well).

Initial screening was done using a diverse collection of 50,000 drug-like compounds from ChemBridge (San Diego, Calif.) obtained as 10 mM stock solutions in DMSO and diluted to 100 mM in 96-well microplates. Structure-activity analysis was done on analogs purchased from ChemBridge and ChemDiv (San Diego, Calif.).

Wildtype and cystic fibrosis (ΔF508 homozygous mutant) mice were bred by the CF Animal Core facility at University of California, San Francisco (UCSF). Animal protocols were approved by the UCSF Committee on Animal Research.

T84 and Caco-2 cells were obtained from the UCSF cell culture facility. T84 cells were cultured in a 1:1 mixture of DMEM and Hams F12 supplemented with 5% fetal calf serum, 100 U/mL penicillin, 100 µg/mL streptomycin and plated on Snapwell inserts (Corning Costar) for growth in a humidified (5% $O_2$/95% $CO_2$) atmosphere at 37° C. Cells were used at 10-14 days after plating. Caco-2 cells were cultured in DMEM containing 10 fetal calf serum, 1% non-essential amino acids, 100 U/mL penicillin and 100 µg/mL streptomycin, and cultured on Snapwell inserts. Cells were used at 21-24 days after plating. Wildtype mice in a CD1 genetic background were bred as described previously. Male Wistar rats (200-250 g) were purchased from Jackson Laboratories. Animal protocols were approved by the UCSF Committee on Animal Research. Fragments of human colon were obtained freshly at the time of excision surgery and transported in ice-cold saline for use within 1 hour after excision.

Forskolin, 8-bromo cGMP, amiloride, cholera toxin and STa toxin were purchased from Sigma Chemical Co. (St. Louis, Mo.). $CFTR_{act}$-16 was from ChemBridge (San Diego, Calif.).

Screening Procedures

Assays were done using a customized screening system (Beckman) consisting of a 3-meter robotic arm, $CO_2$ incubator, plate washer, liquid handling workstation, bar code reader, delidding station, and two FluoStar fluorescence plate readers (BMG Labtechnologies, Offenburg, Germany), each equipped with two syringe pumps and HQ500/20X (500±10 nm) excitation and HQ535/30M (535±15 nm) emission filters (Chroma). The robotic system was integrated using SAMI version 3.3 software (Beckman) modified for two plate readers. Custom software was written in VBA (Visual Basic for Applications) to compute baseline-subtracted, normalized fluorescence slopes (giving halide influx rates) from stored data files.

The assay was set-up by loading the incubator (37° C., 90% humidity, 5% $CO_2$) with 40-60 96-well plates containing the FRT cells, and loading a carousel with 96-well plates containing test compounds and disposable plastic pipette tips. To initiate the assay, each well of a 96-well plate was washed 3 times in PBS (300 µL/wash), leaving 50 µL PBS. Ten µL of a CFTR-activating cocktail (5 µM forskolin, 100 µM IBMX, 25 µM apigenin in PBS) was added, and after 5 min one test compound (0.5 µL of 1 mM DMSO solution) was added to each well to give 10 µM final concentration. After 10 min, 96-well plates were transferred to a plate reader for fluorescence assay. Each well was assayed individually for CFTR-mediated $I^-$ transport by recording fluorescence continuously (200 ms per point) for 2 s (baseline) and then for 12 s after rapid (<0.5 s) addition of 160 µL of isosmolar PBS in which 137 mM $Cl^-$ was replaced by $I^-$.

Assays of Intracellular [cAMP] and Toxicity

[cAMP] and phosphatase assays were performed as reported previously (Galietta et al. 2001 *J. Biol. Chem.* 276: 19723-19728). Cell toxicity was assessed by the dihydrorhodamine method at 24 hours after cell incubation with 0-1000 µM inhibitor. Animal toxicity was assessed by measurement of serum chemistries and hematology (UCSF Clinical Laboratory) in mice at 5 days after daily intraperitoneal injections with 0-100 µg/kg inhibitor.

MDR-1 Activity

MDR-1 activity was evaluated by measuring $^3$H-vincristine accumulation in an immortalized human tracheal cell line, 9HTEo-/Dx, in which the endogenous expression of MDR-1 was upregulated by selection in increasing concentrations of doxorubicin (Rasola et al. 1994 *J. Biol. Chem.* 269:1432-1436). Cells were seeded in 24-well microplates (200,000 cells/well). After 48 hours, cells were washed with a solution containing (in mM): 130 NaCl, 2 KCl, 1 $KH_2PO_4$, 2 $CaCl_2$, 2 $MgCl_2$, 10 Na-Hepes (pH 7.3) and 10 glucose, and incubated for 1 hour at 37° C. with 200 µL of the same solution containing $^3$H-vincristine (0.7 µM; 1 µCi/mL). Cells were then washed three times with ice-cold solution and lysed in 0.25 M NaOH. Vincristine content was determined by scintillation counting.

Short-Circuit Current Tests Using CFTR-Expressing FRT Cells

Snapwell inserts containing CFTR-expressing FRT cells or human bronchial epithelial cells were mounted in an Ussing chamber system. For FRT cells the hemichambers were filled with 5 mL of 75 mM NaCl and 75 mM Na gluconate (apical) and 150 mM NaCl (basolateral) (pH 7.3), and the basolateral membrane was permeabilized with 250 µg/mL amphotericin B (Galietta et al. 2001 *J. Biol Chem.* 276:19723-19728). For bronchial epithelial cells and T84 cells, both hemichambers contained a Krebs bicarbonate solution. Hemichambers were continuously bubbled with air (FRT cells) or 5% $CO_2$ in air (bronchial and T84 cells) and maintained at 37° C. Short-circuit current was recorded continuously using a DVC-1000 voltage clamp (World Precision Instruments, Sarasota, Fla.) using Ag/AgCl electrodes and 1 M KCl agar bridges.

Patch-Clamp Analysis of $Cl^-$ Channel Activity

Membrane current was measured in a whole-cell configuration. For recordings of $Cl^-$ channels, the extracellular (bath) solution contained (in mM): 150 NaCl, 1 $CaCl_2$, 1 $MgCl_2$, 10 glucose, 10 mannitol, 10 TES (pH 7.4), and the intracellular (pipette) solution contained: 120 CsCl, 1 $MgCl_2$, 10 TEA-Cl, 0.5 EGTA, 1 Mg-ATP, 10 Hepes (pH 7.3). CFTR was activated by forskolin (5 µM) in the extracellular solution. The time-course of membrane conductance was monitored in response to alternating voltage pulses of −100 and +80 mV. At defined times the protocol was interrupted to generate current-voltage relationships (voltage pulses from −100 to +100 mV in 20 mV increments). Volume-sensitive $Cl^-$ channels were activated by a hypotonic solution (extracellular NaCl decreased to 120 NaCl; 250 mosM/kg). Calcium-sensitive $Cl^-$ channels were activated in human bronchial epithelial cells by addition of 100 µM UTP to the extracellular solution.

Patch-Clamp Analysis of ATP-Sensitive $K^+$ Channels

Membrane potential was recorded in the pancreatic β cell line INS-1 in which the extracellular (bath) solution contained (in mM): 130 NaCl, 2 KCl, 1 $KH_2PO_4$, 2 $CaCl_2$, 2 $MgCl_2$, 10 Na-Hepes (pH 7.3) and 10 glucose. The pipette contained (in mM): 140 KCl, 1 $CaCl_2$, 2 mM $MgCl_2$, 10 EGTA, 0.5 MgATP, 10 K-Hepes (pH 7.3). After achieving the whole-cell configuration, the amplifier was switched to current-clamp mode.

Intestinal Fluid Secretion and Short-Circuit Current

In the first of 3 assays, fluid accumulation in ileal loops was measured (Oi et al. 2002 *Proc. Natl. Acad. Sci. USA* 99:3042-3046; Gorbach et al. 1971 *J. Clin. Invest.* 50:881-889). Mice (age 8-10 weeks, body weight 25-35 g) in a CD1 genetic background (or ΔF508 homozygous mice) were starved for 24 hrs and anaesthetized with intraperitoneal ketamine (40 mg/kg) and xylazine (8 mg/kg). Body temperature was maintained during surgery at 36-38° C. using a heating pad. A small abdominal incision was made to expose the small intestine and closed ileal loops (length 20-30 mm) proximal to the cecum were isolated by sutures. Loops were injected with 100 µL of PBS alone or PBS containing cholera toxin (1 µg). In some experiments the inhibitor (150 µg/kg) was administered by intraperitoneal injection. The abdominal incision was closed with suture and mice were allowed to recover from anesthesia. At 6 hours the mice were anesthetized, intestinal loops were exteriorized, and loop length and weight were measured after removal of mesentery and connective tissue.

In the sealed adult mouse model of secretory diarrhea mice were gavaged with cholera toxin (10 µg) in 0.1 mL of 7% bicarbonate buffer (or buffer alone) using a orogastric feeding needle (Richardson et al 1986 Infect. Immun. 54:522-528; Gabriel et al 1999 Am J. Physiol. 276:G58-G63). Four experimental groups were: control (buffer alone), cholera-treated, cholera-treated+inhibitor (150 µg/kg intraperitoneal 2 min before gavage), and inhibitor alone. After six hours mice were euthanized and the small intestine (from pylorus to cecum) was exteriorized and stripped of associated mesenteric and connective tissues. The intestine was weighed, then opened longitudinally to remove lumenal fluid (by blotting), and weighed again. Fluid accumulation was computed from the ratio in intestinal weight before and after lumenal fluid removal. For measurement of short-circuit current, strips of rat colon were isolated, stripped of muscle layers by blunt dissection, mounted in Ussing chambers (area 0.7 cm$^2$), and bathed in oxygenated bicarbonate Ringers solution containing 10 µM indomethacin. Short-circuit current was measured after inhibition of Na$^+$ current by amiloride (10 µM), followed by stimulation by forskolin (20 µM) and subsequent inhibitor addition.

Figure 6:
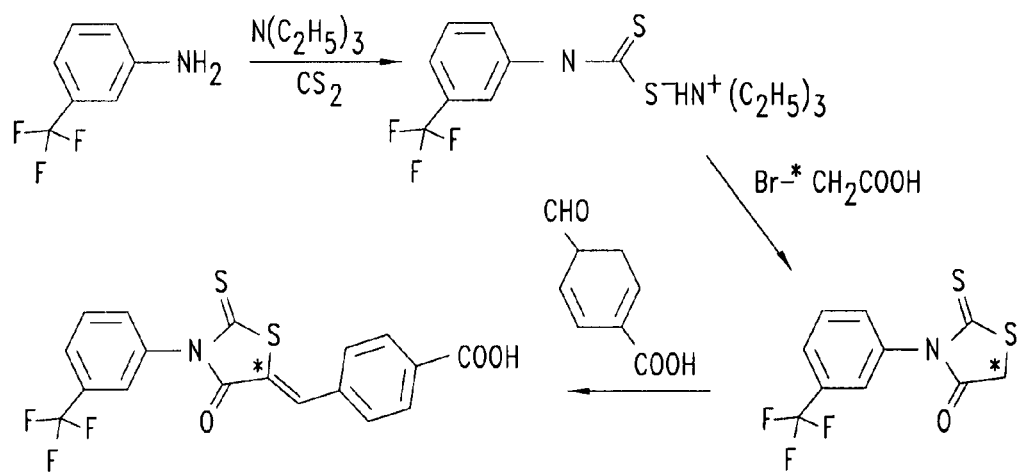
FIG. 6 is a schematic showing synthesis of $^{14}$C-labeled $CFTR_{inh}$-172. $^{14}$C was incorporated into the thiazolidinone core using $^{14}$C-labeled Br-acetic acid as starting material.

Synthesis of $^{14}$C-Labeled CFTR$_{inh}$-172 (FIG. 6)

The intermediate 2-thioxo-3-(3-trifluoromethyl phenyl)-4-thiazolidinone was synthesized by dropwise addition of carbon disulfide (0.8 g, 10 mM) to a stirred solution of 3-trifluoromethylaniline (1.6 g, 10 mM) and triethylamine (1 g, 10 mM) in ethyl acetate (10 mL) over 30 minutes. An ice bath was used to prevent excessive heating during reaction. After stirring overnight, the thick yellow slurry was filtered and the precipitate was washed with 50 mL of ether and air dried to give 3 g (89% yield) of a pale yellow dithiocarbamate solid (melting point 92-95° C.). Na Br—$^{14}$C-acetate (prepared from Br—$^{14}$C-acetic acid (Amersham), 55 mCi/mmol, 64 mg, 0.46 mM in 0.6 mL of water, pH 8-9 using NaHCO$_3$) was stirred and cooled to 5-10° C. and dithiocarbamate (0.3 g, 0.9 mM) was added over 10 minutes. Stirring was continued while the flask was allowed to warm to ambient temperature. After 2 hours, the solution was cooled to 10° C., acidified with concentrated HCl, and heated to 90-95° C. for 30 minutes. The resultant precipitate was filtered, washed with water and recrystallized from ethanol to give 103 mg of the desired product as shiny crystals (83% yield), m.p. 177-178° C.; specific activity ($^{14}$C) 55 mCi/mmol; $^1$H NMR (300 MHz, CDCl$_3$): δ 4.18 (s, 2H, CH$_2$), 7.40 (d, 1H, phenyl, J=8.0 Hz), 7.48 (s, 1H, phenyl), 7.64 (t, 1H, phenyl, J=8.0 Hz), 7.72 (d, 1H, phenyl, J=7.6 Hz) ppm.

For synthesis of 2-thioxo-3-(3-trifluoromethylphenyl)-5-[4-carboxyphenylmethylene]-4-thiazolidinone ($^{14}$C-5) ($^{14}$C-CFTR$_{inh}$-172), a mixture of 2-thioxo-3-(3-trifluoromethylphenyl)-4-thiazolidinone ($^{14}$C-5) (100 mg, 0.36 mM) and 4-carboxybenzaldehyde (54 mg, 0.36 mM) in absolute alcohol (1 mL) and piperidine (1 drop) was refluxed for 30 minutes. The yellow precipitate was filtered, washed with ethanol, dried and recrystallized from ethanol to give 108 mg (73% yield) yellow crystals, m.p. 180-182° C.; specific activity ($^{14}$C) 54 mCi/mmol; $^1$H NMR (300 MHz, DMSO-d$_6$): δ 7.78 (d, 2H, carboxyphenyl, J=8.2 Hz), 7.80-8.00 (m, 5H, trifluoromethylphenyl and CH), 8.07 (d, 2H, carboxyphenyl, J=8.31 Hz), 13.20 (s, 1H, COOH, D$_2$O exchange) ppm. Purification to >99.9% was accomplished by repeated recrystallization.

Pharmacokinetic Studies

A bolus of $^{14}$C-CFTR$_{inh}$-172 (50 µCi) in PBS containing 3% DMSO (titrated to pH 7.4 using NaOH) was administered intravenously in rats over 1 min (male Sprague-Dawley rats, 360-420 grams) by an indwelling jugular catheter. Blood was collected from the catheter at specified times. $^{14}$C-Radioactivity was determined in plasma (isolated by centrifugation of whole blood at 14,000 g for 10 min) by scintillation counting (Scintiverse SE, Fisher, Calif.) using a LS-6500 Multi-Purpose Scintillation Counter (Beckman). Pharmacokinetic analysis was done using WinNonLin software (Pharsight). Rats were sacrificed by pentabarbital overdose after collection of the final blood/tissue samples. All animal procedures were approved by the UCSF Committee on Animal Research.

Tissue Distribution and Elimination Studies

A bolus of $^{14}$C-CFTR$_{inh}$-172 (2 µCi) was administered intravenously over 1 min in mice (male CD1 mice, 30-35 grams) by tail vein. Mice were sacrificed at 5, 30, 120 and 240 min. Organs were removed, weighed and homogenized in distilled water (10-50 vol %). Radioactivity was determined by scintillation counting of the homogenates (25-50 µL) and expressed as total $^{14}$C-radioactivity per organ (or per gram tissue for skeletal muscle). At the same time blood, urine and bile (from gallbladder or duodenum) were collected and $^{14}$C-radioactivity was measured and expressed per mL of fluid. Elimination studies were done by collections of urine and stool over the first 24 hr after $^{14}$C-CFTR$_{inh}$-172 administration. Tissue distribution studies were also done on rats prepared as for pharmacokinetic studies.

Analysis of Inhibitor Metabolism

Aliquots of bodily fluids (plasma, urine, bile) and liver homogenate were spotted onto Silica plates and resolved by thin layer chromatography using a ethyl acetate hexane: methanol (1:1:0.1) solvent system which gave rf ~0.5 for the original inhibitor. Autoradiography was performed using Hyperfilm (Amersham) with a Transcreen LE amplification system (Kodak). $^{14}$C-labeled CFTR$_{inh}$-172 standards were included on all plates.

Short-Circuit Current Measurements

Examples 7

For cell studies, Snapwell inserts containing T84 cell monolayers were mounted in an Ussing chamber system (Navicyte, Harvard Apparatus, Holliston, Mass.). Hemichambers were filled with Krebs-bicarbonate solution containing (in mM) NaCl 120, NaHCO$_3$ 25, KH$_2$PO$_4$ 3.3, K$_2$HPO$_4$ 0.8, MgCl$_2$ 1.2, CaCl$_2$ 1.2, glucose 10 (maintained at 37° C.) and continuously bubbled with 5% CO$_2$/95% O$_2$. High K$^+$ buffer contained (in mM) NaCl 65, KCl 67.5, KH$_2$PO$_4$ 1.5, CaCl$_2$ 1, MgCl$_2$ 0.5, HEPES 10, glucose 10. Low Cl$^-$ buffer contained (in mM) Na-gluconate 120, KH$_2$PO$_4$ 3.3, K$_2$HPO$_4$ 0.8, MgCl$_2$ 1.2, CaCl$_2$ 1.2, HEPES 10, glucose 10 (maintained at 37° C.) and continuously bubbled with air. For measurements in mouse colon, mice were anaesthetized with intraperitoneal ketamine (40 mg/kg) and xylazine (8 mg/kg). The ileum was removed, washed with ice-cold Krebs buffer, opened along the mesenteric border, and mounted in a micro-Ussing chamber (area 0.7 cm$^2$, World Precision Instruments, Sarasota, Fla.). For measurements in human intestine, colonic fragments were stripped of muscle layers by blunt dissection and mounted as described above. Hemichambers were filled with oxygenated Ringers bicarbonate solution containing 10 μM indomethacin. Short-circuit current was recorded using a DVC-1000 voltage-clamp (World Precision Instruments) with Ag/AgCl electrodes and 1 M KCl agar bridges. Agonists/inhibitors were added to hemichambers as described below.

In Vivo Intestinal Fluid Secretion in Mouse and Rat Models

Examples 5 and 7

Mice (age 8-10 weeks, body weight 25-35 g) in a CD1 genetic background were given access to water but not food for 24 hr. Mice were anaesthetized as described above and body temperature was maintained during surgery at 36-38° C. using a heating pad. A small abdominal incision was made to expose the small intestine and closed ileal loops (length 20-30 mm) proximal to the cecum were isolated by sutures. Loops were injected with 100 μL of PBS alone or PBS containing cholera toxin (1 μg). In some experiments $CFTR_{inh}$-172 (0-200 μg) was administered by intraperitoneal injection at specified times before or after cholera toxin injection. The abdominal incision was closed with suture and mice were allowed to recover from anesthesia. At 6 hours the mice were anesthetized, intestinal loops were exteriorized, and loop length and weight were measured after removal of mesentery and connective tissue.

For measurement of enterotoxin-induced fluid secretion in a rat closed-loop model, male Wistar rats (body weight 200-250 g) were anesthetized with pentobarbital sodium (45 mg/kg). Loops (40-60 mm) were isolated and injected with 300 μL PBS alone or PBS containing cholera toxin (10 μg) or STa toxin (0.1 μg). In some experiments $CFTR_{inh}$-172 (200 μg) was given by intraperitoneal injection after cholera toxin or STa toxin administration. Loop length and weight were measured at 3 hr (STa) or 6 hr (cholera toxin).

In studies of orally administered $CFTR_{inh}$-172, an open-loop mouse model was used in which mice were gavaged with 7% bicarbonate buffer or cholera toxin (1 μg in 7% bicarbonate buffer) alone and with $CFTR_{inh}$-172 (200 μg in vitamin E TPGS, see below) using an orogastric feeding needle. After 6 hours the small intestine (from pylorus to cecum) was exteriorized and stripped of associated mesenteric and connective tissue. The intestine was weighed, opened longitudinally to remove lumenal fluid, and reweighed to quantify fluid accumulation.

Caco-2 Permeability Assay.

Caco-2 cells were cultured on porous inserts to give monolayer resistances of 400-600 Ωcm$^{-1}$. For transport studies culture medium was replaced with an equal volume of Hank's buffered salt solution (HBSS) containing 15 mM glucose and 25 mM HEPES (pH 7.3). After 1 hr $CFTR_{inh}$-172 (25 μM) was added to the upper chamber and plates were gently rocked at 37° C. At specified times 50 μL of solution from the lower (receiving) chamber were removed for measurement of $CFTR_{inh}$-172 concentration by UV absorbance (385 nm). Apparent permeability (Papp) was calculated from: Papp=dC/dT×(Vr/AC0), where dC/dT is the rate of increase in $CFTR_{inh}$-172 concentration in the receiver chamber, Vr is the volume of the receiver chamber, A is monolayer surface area, and C0 is initial $CFTR_{inh}$-172 concentration in the donor chamber.

Pharmacokinetic and Oral Bioavailability Studies.

Mice were anesthetized briefly using halothane and gavaged orally with $^{14}$C-labeled $CFTR_{inh}$-172 (12 μCi) solubilized with vitamin E TPGS (d-α-tocopheryl polyethylene glycol 1000 succinate, 0.5% w/v) $CFTR_{inh}$-172 in 10% w/v suspension of TPGS in water). For comparison other mice were given $^{14}$C-$CFTR_{inh}$-172 (2 μCi) intravenously by tail vein infusion. Blood was collected from the tail vein at specified times for measurement of plasma $^{14}$C radioactivity. At 6 hours mice were killed by pentobarbital overdose and organs were removed for measurement of radioactivity in homogenates.

Biological Example 1

Screening of CFTR Inhibitors

The primary screening technique used to identify the compounds of the invention was designed to identify inhibitors of CFTR Cl$^-$ conductance by direct CFTR-inhibitor interaction. CFTR was pre-stimulated in CFTR-expressing FRT cells by an activating cocktail containing forskolin, IBMX and apigenin, as shown schematically in FIG. 1A. The activation of CFTR by multiple mechanisms (cAMP elevation, phosphodiesterase inhibition, and direct CFTR binding) allowed identification of inhibitors that blocked the CFTR Cl$^-$ transporting pathway directly rather than more proximal step(s) in a signaling pathway. The FRT cells co-expressed a yellow fluorescent protein-based Cl$^-$/I$^-$ sensor that provided a quantitative fluorescence read-out of inhibition potency (See, e.g., Jayaraman et al., 2000, *J. Biol. Chem.* 275:6047-6050; Galietta et al., 2001, *Am. J. Physiol.* 281:C1734-C1742). After CFTR pre-stimulation and compound addition, cells were subjected to an inwardly-directed I$^-$ gradient to drive I$^-$ influx and produce decreasing fluorescence. Each assay consisted of recording baseline fluorescence for 2 seconds, followed by 12 seconds of continuous recording of fluorescence after rapid addition of the I$^-$ containing solution. Compounds were tested separately at 10 μM concentration in a 96-well format utilizing a fully-automated high-throughput screening apparatus (see Example 2 below).

Figure 1B:
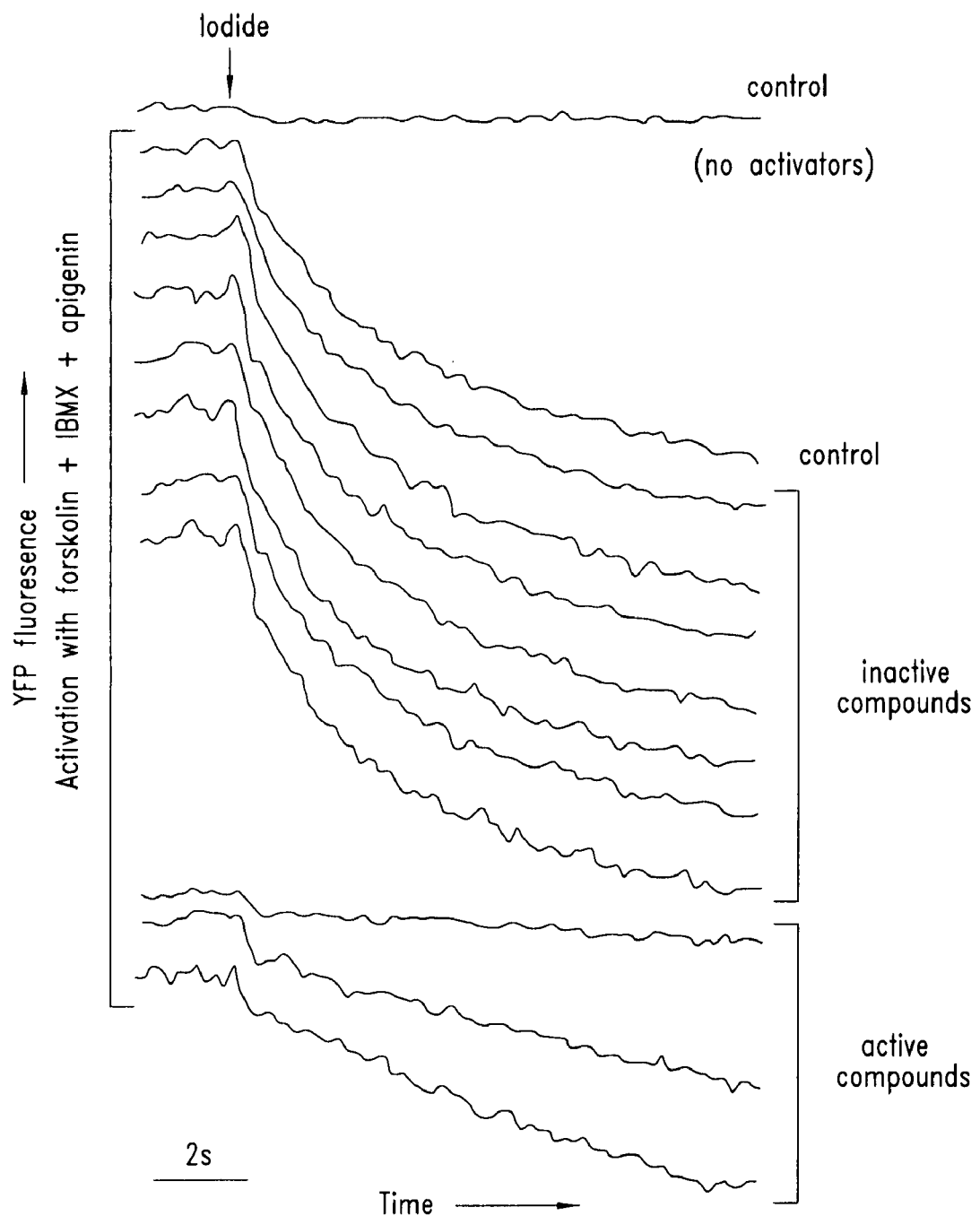
FIG. 1B is a graphical illustration of representative fluorescence data from individual wells using the screening technique of FIG. 1A, showing controls (no activator, no test compound), inactive compounds and active CFTR inhibitor compounds.
Figure 1C:
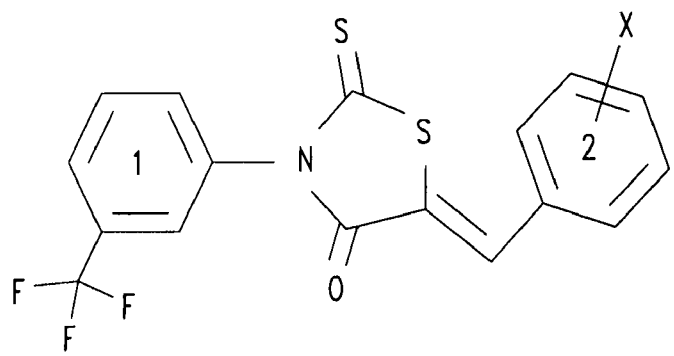
FIG. 1C shows chemical structures of CFTR inhibitors identified by the screening technique of FIG. 1A.

FIG. 1B graphically illustrates representative curves, as relative YFP fluorescence versus time, from the primary screen of 50,000 compounds using the assay of FIG. 1A. As quantified from the slope of the decreasing fluorescence after I$^-$ addition, 49,993 compounds had no significant effect on the kinetics of I$^-$ influx (<10% decrease in slope). Seven compounds produced a small decrease in negative slope (10-52%), nearly all of which had a similar core structure consisting of a 2-thioxo-4-thiazolidinone heterocycle with substituted phenylmethylene and phenyl moieties (FIG. 1C). More than 250 analogs having thiazolidinone core structure were subsequently screened to identify the most potent CFTR inhibitors.

Figure 1D:
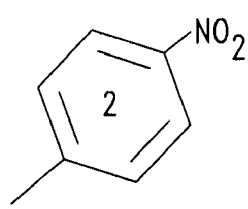
FIG. 1D shows chemical structures of Ring 2 of the thiazolidinone derivatives having the greatest CFTR inhibitory activity. The complete thiazolidinone derivative structure is shown in FIG. 1C. Relative potencies were: 0.2 ($CFTR_{inh}$-020), 0.3 ($CFTR_{inh}$-029), 1.0 ($CFTR_{inh}$-172), 0.2 ($CFTR_{inh}$-185), 0.1 ($CFTR_{inh}$-214) and 0.1 ($CFTR_{inh}$-236).
Figure 1D:
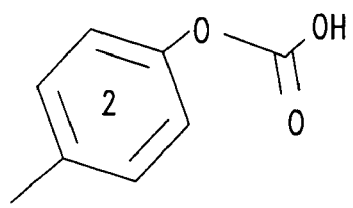
Figure 1D:
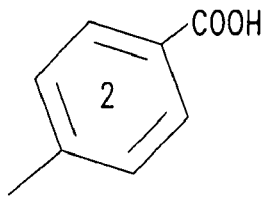
Figure 1D:
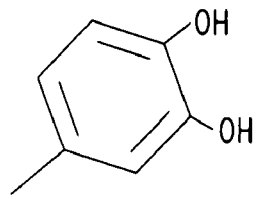
Figure 1D:
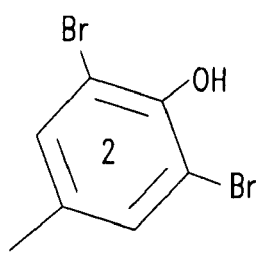
Figure 1D:
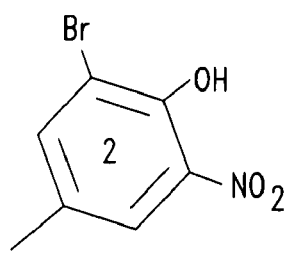

FIG. 1D shows the most effective thiazolidinone CFTR inhibitors identified in the screening were 3-[(3-trifluoromethyl)phenyl]-5-[(4-carboxyphenyl)methylene]-2-thioxo-4-thiazolidinone (referred to herein as $CFTR_{inh}$-172), along with five analogs having significant inhibitory potencies. Thus the following compounds were identified as CFTR inhibitors: 3-[(3-trifluoromethyl)phenyl]-5-[(4-carboxyphenyl)methylene]-2-thioxo-4-thiazolidinone ($CFTR_{inh}$-172); 3-[(3-trifluoromethyl)phenyl]-5-[(4-nitrophenyl)methylene]-2-thioxo-4-thiazolidinone ($CFTR_{inh}$-020); 3-[(3-trifluoromethyl)phenyl]-5-[(4-oxycarboxyphenyl)methylene]-2-thioxo-4-thiazolidinone ($CFTR_{inh}$-029); 3-[(3-trifluoromethyl)phenyl]-5-[(3,4-dihydroxyphenyl)

methylene]-2-thioxo-4-thiazolidinone (CFTR$_{inh}$-185), 3-[(3-trifluoromethyl)phenyl]-5-[(3,5-dibromo-4-hydroxyphenyl)methylene]-2-thioxo-4-thiazolidinone (CFTR$_{inh}$-214) and 3-[(3-trifluoromethyl)phenyl]-5-[(3-bromo-4-hydroxy-5-nitrophenyl)methylene]-2-thioxo-4-thiazolidinone (CFTR$_{inh}$-236). The most effective CFTR inhibitors included one or more electron-withdrawing groups, such as a 3-trifluoromethyl group, on ring 1, and electron-withdrawing group or polar substituents on ring 2 as discussed above. CFTR$_{inh}$-172 was selected for further analysis. The relative potencies were: 0.2 (CFTR$_{inh}$-020), 0.3 (CFTR$_{inh}$-029), 1.0 (CFTR$_{inh}$-172), 0.2 (CFTR$_{inh}$-185), 0.1 (CFTR$_{inh}$-214), and 0.1 (CFTR$_{inh}$-236).

To examine the effect of ring position of the trifluoromethyl and carboxyl substituents, 8 analogs of CFTR$_{inh}$-172 were synthesized in which the substituents were moved to each unique position on rings 1 (trifluoromethyl) and 2 (carboxy). Compared to CFTR$_{inh}$-172 (potency 1.0), the relative inhibitory potencies of the 3-[(a-trifluoromethyl)phenyl]-5-[(b-carboxyphenyl)methylene]-2-thioxo-4-thiazolidinone analogs were: 0.69 (a=2, b=2), 0.70 (2, 3), 0.66 (2, 4), 0.74 (3, 2), 0.90 (3, 3), 0.67 (4, 2), 0.64 (4, 3) and 0.56 (4, 4).

Biological Example 2

Characterization of CFTR$_{inh}$-172

Figure 2A:
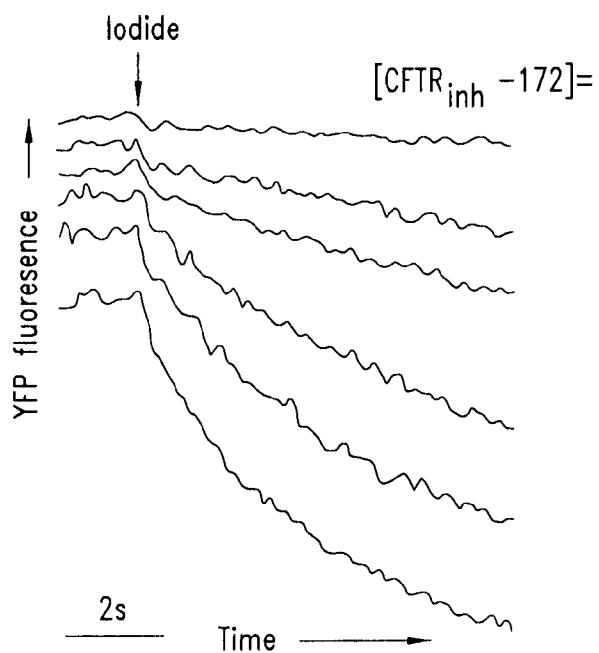
FIG. 2A is a graphical representation of relative fluorescence versus time using the screening technique of FIG. 1A for the CFTR inhibitor 3-[(3-trifluoromethyl)phenyl]-5-[(4-carboxyphenyl)methylene]-2-thioxo-4-thiazolidinone (referred to herein as $CFTR_{inh}$-172) at several concentrations.
Figure 2B:
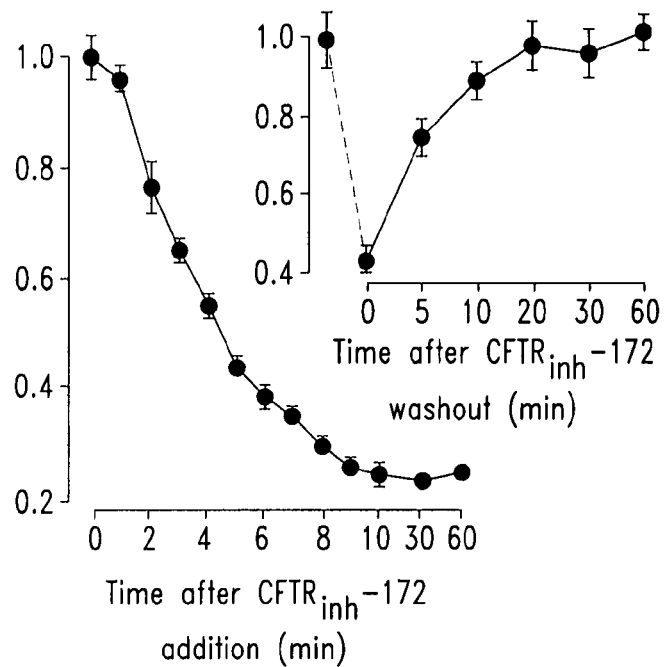
FIG. 2B is a graphical representation of the time course of inhibition showing CFTR-mediated I$^-$ transport rates at different times after addition of 2 µM $CFTR_{inh}$-172. The inset is a graphical representation of the time course of inhibition reversal showing I$^-$ transport rates at different times after washout of 1 µM $CFTR_{inh}$-172. Mean±SE from three sets of experiments.
Figure 2C:
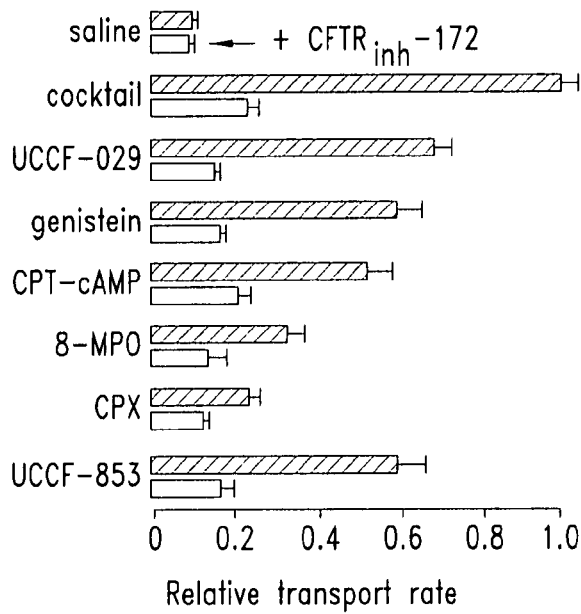
FIG. 2C is a graphical representation of inhibition of CFTR after stimulation by different agonists, including benzoflavone and benzimidazolone UCcF compounds ($UC_{CF}$-029 (2-(4-pyridinium)benzo[h]-4H-chromen-4-one bisulfate) and $UC_{CF}$-853 (Galietta et al. 2001 *J. Biol. Chem.* 276:19723-19728)), genistein, CPT-cAMP, 8-methoxypsoralen (8-MPO), 8-cyclopentyl-1,3-dipropylxanthine (CPX) (all 50 µM) (±SE from three sets of experiments). Filled bars show agonist, and open bars show agonist with 5 µM $CFTR_{inh}$-172.

The level of CFTR inhibition for specific dosages of the subject thiazolidinone compounds was determined using the fluorescence assay shown in FIG. 1A and described above. FIG. 2A shows dose-inhibition data for CFTR$_{inh}$-172 as relative YFP fluorescence versus time. Significant CFTR inhibition was seen at 0.3-0.6 μM concentrations of this thiazolidinone compound. FIG. 2B shows that inhibition by CFTR$_{inh}$-172 (shown graphically as relative transport rate versus time after addition or washout) was complete in ~10 min ($t_{1/2}$ 4 min) and was reversed after washout with $t_{1/2}$ ~5 min (inset). The relative transport rates illustrated in FIG. 2C show that CFTR$_{inh}$-172 effectively inhibited CFTR activation by multiple types of agonists that were not included in the activating cocktail used for initial screening. These agonists included genistein, CPT-cAMP, CPX, 8-MPO and the potent benzoflavone CFTR activator UC$_{CF}$-029 (2-(4-pyridinium)benzo[h]4H-chromen-4-one bisulfate) and the benzimidazolone CFTR activator UC$_{CF}$-853 (see Galietta, et al., 2001, *J. Biol. Chem.* 276:19723-19728).

Figure 3A:
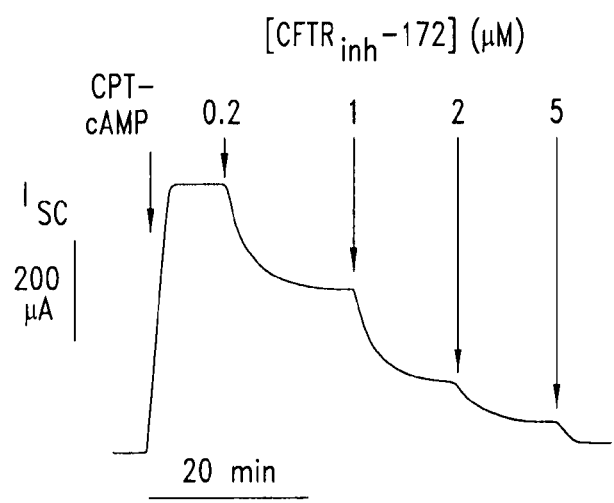
FIG. 3A is a graphical representation of $CFTR_{inh}$-172 inhibition of short-circuit current in permeabilized FRT cells expressing human CFTR. CFTR was stimulated by 100 µM CPT-cAMP.
Figure 3B:
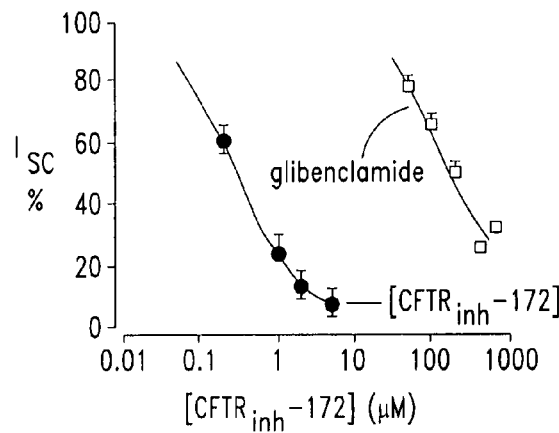
FIG. 3B graphically provides a summary of dose-inhibition data for $CFTR_{inh}$-172 (circles) and glibenclamide (squares) (SE, three sets of experiments).

Electrophysiology experiments were also carried out to establish the inhibitory potency and specificity of CFTR$_{inh}$-172. FIG. 3A shows the rapid, dose-dependent inhibition of short-circuit current in CFTR-expressing FRT cells with CFTR$_{inh}$-172 added to the solution bathing the apical cell surface. FIG. 3B shows the average dose-inhibition relationships of CFTR$_{inh}$-172 ($K_d$ ~300 nM, Hill coefficient ~1) and glibenclamide ($K_d$ ~200 μM) tested under identical conditions.

Figure 3C:
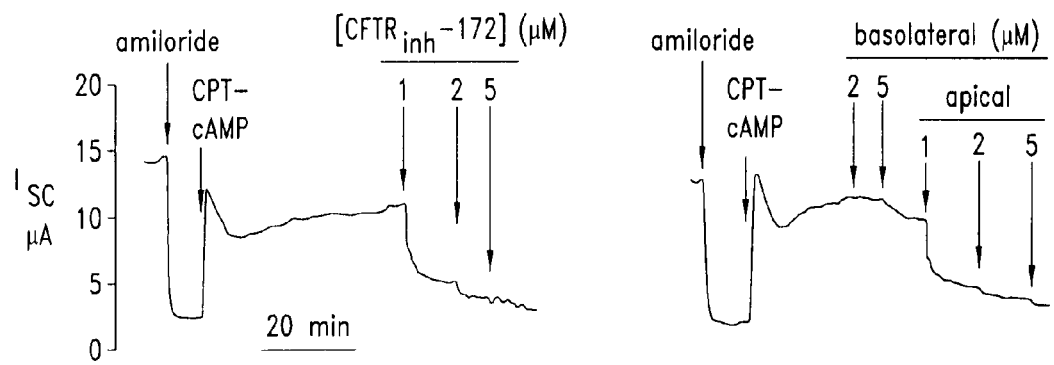
FIG. 3C graphically illustrates $CFTR_{inh}$-172 inhibition of short-circuit current in primary culture of (non-permeabilized) human bronchial epithelial cells. Inhibitor was added in apical bathing solution (left panel) or basolateral and then apical solutions (right panel).

Similar inhibitory potencies for this thiazolidinone were found in cells that natively express wildtype CFTR, including T84 cells and primary cultures of human bronchial epithelial cells, as well as in transfected FRT cells expressing G551D-CFTR and ΔF508-CFTR (after low temperature correction). For studies in bronchial cells, the Na$^+$ channel was blocked with amiloride so that baseline current is largely CFTR-dependent. After maximal CFTR activation by a CPT-cAMP, application of CFTR$_{inh}$-172 from the apical side inhibited short-circuit current strongly (FIG. 3C, left). CFTR$_{inh}$-172 also inhibited short-circuit current when added from the basolateral side (FIG. 3C, right).

Whole-cell membrane currents were measured in CFTR-expressing FRT cells as shown in FIG. 3D. Stimulation by 5 μM forskolin produced a membrane current of 381±47 pA/pF (n=4) at +100 mV (total membrane capacitance 21±3 pF). The current-voltage relationship was linear as expected for a pure CFTR current (FIG. 3F). Extracellular perfusion with 2 μM CFTR$_{inh}$-172 produced a rapid reduction in current at all membrane potentials, suggesting voltage-independent CFTR inhibition. The lack of voltage-dependence of channel block was confirmed using a lower concentration of CFTR$_{inh}$-172 (0.2 μM) to obtain 50% inhibition (FIG. 3F).

Figure 4A:
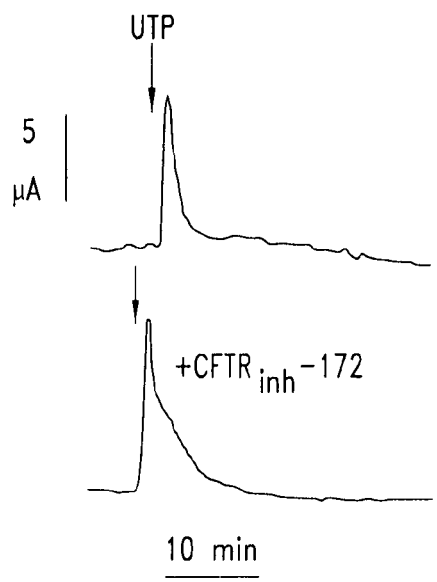
FIG. 4A is a graphical representation of UTP—(100 µM) stimulated $Ca^{2+}$-dependent Cl$^-$ secretion measured in short-circuit current measurements on airway epithelial cells in the absence and presence of 5 µM of $CFTR_{inh}$-172.
Figure 4B:
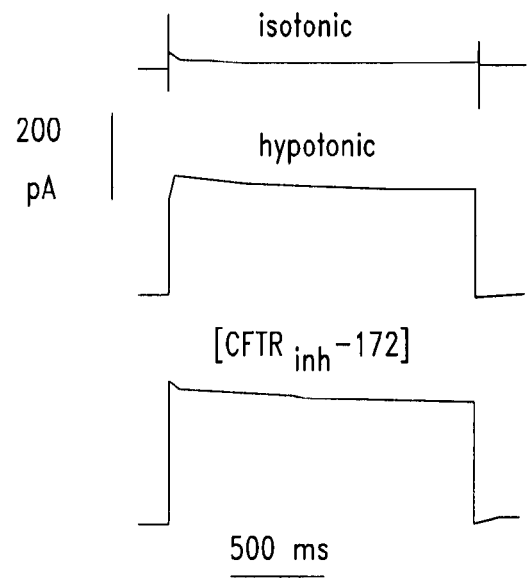
FIG. 4B is a graphical representation of volume-activated Cl$^-$ current (hypotonic 250 mosM/kg $H_2O$) measured in whole-cell patch clamp experiments on FRT cells. Currents were recorded in the absence and presence of 5 µM $CFTR_{inh}$-172.

The specificity of CFTR$_{inh}$-172 for inhibition of CFTR was also examined. Two non-CFTR Cl$^-$ channels were studied. CFTR$_{inh}$-172 at 5 μM concentration did not inhibit Ca$^{2+}$ activated Cl$^-$ secretion produced by addition of UTP (100 μM) to the apical bathing solution in polarized human bronchial epithelial cells (FIG. 4A). Maximal UTP-dependent short-circuit currents were 9.9±0.5 μA/cm$^2$ and 10.0±0.2 μA/cm$^2$ in the absence and presence of CFTR$_{inh}$-172, respectively (SE, n=4). CFTR$_{inh}$-172 at 5 μM also did not block volume-activated Cl$^-$ currents elicited in FRT cells by extracellular perfusion with a 250 mosM/kg hypotonic solution (FIG. 4B).

Figure 4C:
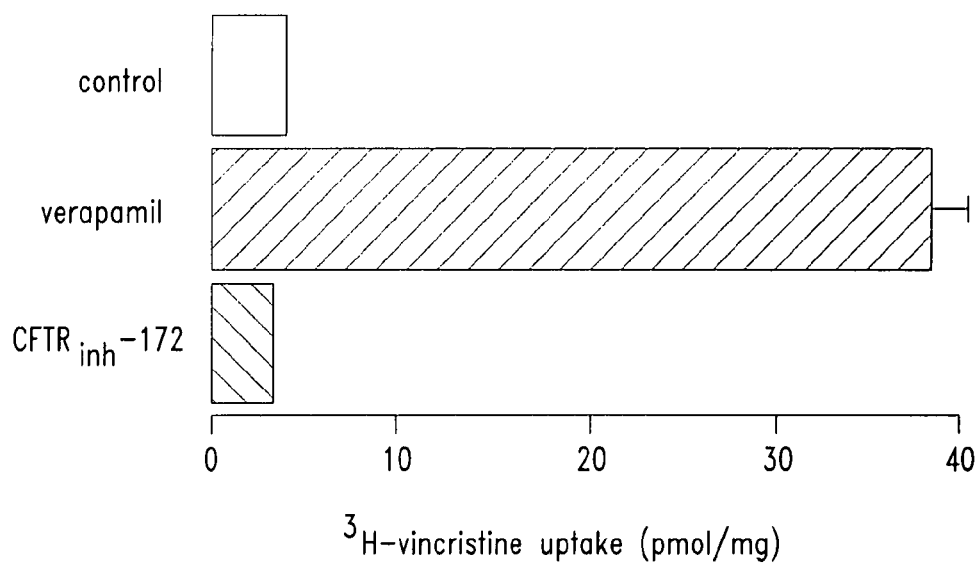
FIG. 4C is a graphical representation of $^3$H-vincristine accumulation in 9HTEo-/Dx cells with upregulated MDR-1 expression. Intracellular vincristine was measured with and without verapamil (100 µM) or $CFTR_{inh}$-172 (5 µM) (SE, n=3).

The activity of a CFTR homolog, the ATP-binding cassette transporter MDR-1 (multi-drug resistance protein-1), was measured in 9HTEo-/Dx which overexpress MDR-1 (Rasola et al. 1994 *J. Biol. Chem.* 269:1432-1436). Vincristine accumulation, which is inversely related to active drug extrusion by MDR-1, was strongly increased by the MDR-1 inhibitor verapamil (100 μM) (FIG. 4C). CFTR$_{inh}$-172 (5 μM) did not affect vincristine accumulation and thus did not inhibit MDR-1.

Figures 4D, 4E:
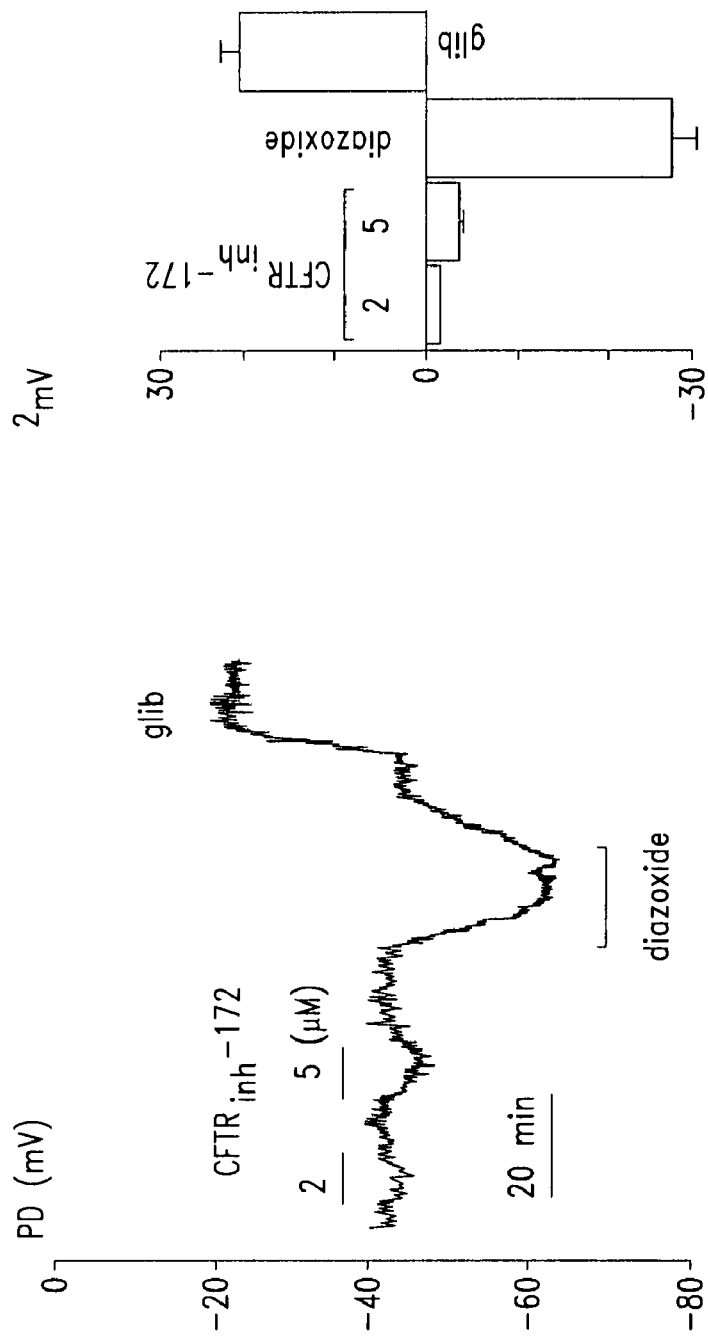
FIG. 4D is a graphical illustration showing a representative membrane potential recording from a pancreatic β cell (INS-1) perfused extracellularly with $CFTR_{inh}$-172, diazoxide (100 µM), and glibenclamide (10 µM).
FIG. 4E is a graphical representation of averaged changes in membrane potential (ΔmV) caused by maneuvers indicated in FIG. 4D (SE, n=4).

Another homolog of CFTR is the sulphonylurea receptor (SUR) which regulates the activity of ATP-sensitive K$^+$ channels (K-ATP channel) (Aguilar-Bryan and Bryan 1999 *Endocr. Rev.* 20:101-135). SUR1 is expressed in pancreatic β-cells where it controls membrane potential and insulin release. Sulphonylureas, like glibenclamide, cause insulin release (and a hypoglycemic response) by blocking K-ATP channels and membrane depolarization. To determine whether CFTR$_{inh}$-172 also blocks K-ATP channels, membrane potential in a rat pancreatic β cell line, INS-1, was measured (FIG. 4D, FIG. 4E). In contrast to large membrane depolarization caused by glibenclamide, CFTR$_{inh}$-172 (2 and 5 μM) did not depolarize membrane potential. CFTR$_{inh}$-172 at 5 μM caused a small hyperpolarization that was much less than that caused by the K-ATP channel activator diazoxide (100 μM). Additional studies indicated that CFTR$_{inh}$-172 at 5 μM did not block a water channel (AQP1), urea transporter (UT-B), Na$^+$/H$^+$ exchanger (NHE3) and Cl$^-$/HCO$_3^-$ exchanger (AE1).

Further analysis showed that 5 μM CFTR$_{inh}$-172 did not affect cellular cAMP production or phosphatase activity. In FRT cells, basal cAMP content was 225±22 fmol/well, which increased at 30 min after stimulation by 20 μM forskolin to 1290±190 fmol/well (no inhibitor) and 1140±50 (+CFTR$_{inh}$-172) (n=3). As judged using the dihydrorhodamine assay, CFTR$_{inh}$-172 was non-toxic to FRT cells after 24 hours at concentrations up to 100 μM. In mice, intraperitoneal injection of 1000 μg/kg CFTR$_{inh}$-172 daily for 7 days did not cause overt toxicity. Food and water intake were not diminished, and serum electrolyte concentrations, glucose, liver function indices, serum creatinine, amylase and hematocrit were not changed. In addition, a single very large systemic dose of CFTR$_{inh}$-172 (10 mg/kg) did not cause overt toxicity.

Biological Example 3

In Vivo Efficacy

Figure 5A:
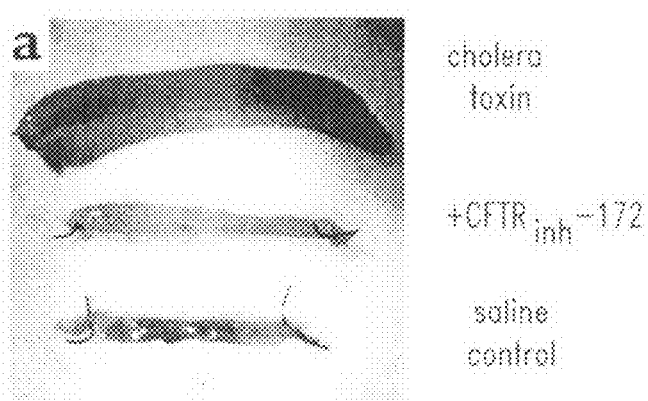
FIG. 5A is a photograph of isolated mouse ileal loops at six hours after lumenal injection of 1 µg cholera toxin without (top) and with (middle) intraperitoneal injection of $CFTR_{inh}$-172 (150 µg/kg). A saline control (no cholera toxin, bottom) is shown for comparison.

The efficacy of CFTR$_{inh}$-172 was tested in vivo using two assays of cholera toxin-induced intestinal fluid secretion, and in isolated intestine by short-circuit analysis. In the first assay, a series of closed loops of small intestine were created in vivo and the lumens of alternate loops were injected with small volumes of saline or saline containing cholera toxin. Luminal fluid accumulation was determined after 6 hours. As seen visually in FIG. 5A, there was marked fluid accumulation and distention in cholera toxin-treated loops, whereas adjacent control (saline) loops remained empty. A single administration of CFTR$_{inh}$-172 (150 µg/kg intraperitoneal) prior to cholera toxin infusion effectively prevented fluid accumulation in the toxin-treated intestinal loops.

Figure 5B:
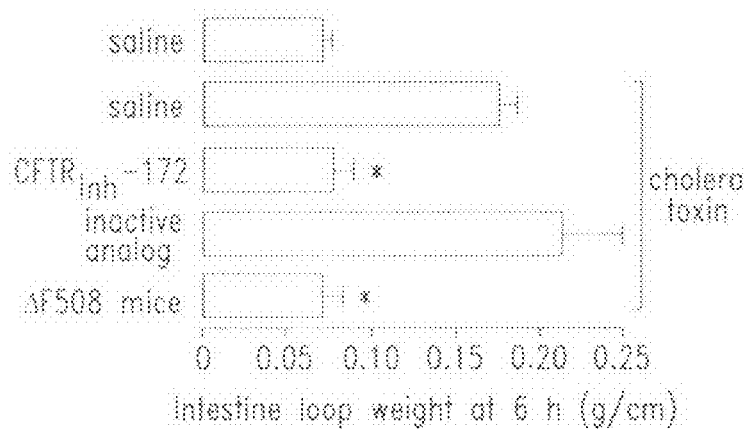
FIG. 5B graphically illustrates ileal loop weight at six hours, with a mean±SE (n=6-8 mice) with 14-16 loops studied. For the inactive analog, the 4-carboxyphenyl group in $CFTR_{inh}$-172 was replaced by 3-methoxy-4-methoxyvinylphenyl (SE, 6-8 mice per group, * p<0.001, ANOVA).
Figure 5C:
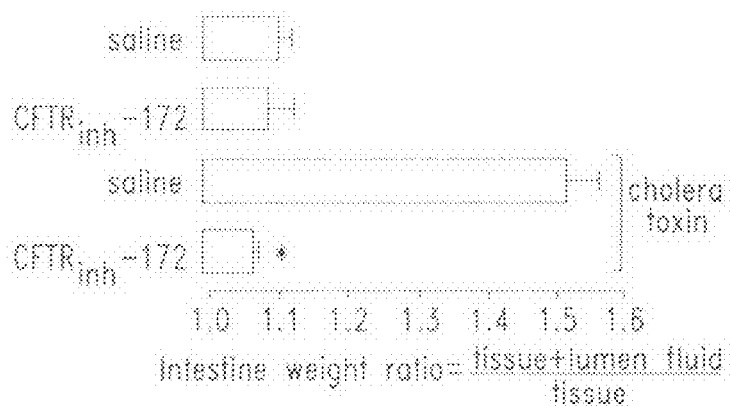
FIG. 5C graphically illustrates the ratio of weight of entire small intestine at six hours after oral gavage before vs. after luminal fluid removal (SE, 4 mice per group, p<0.001).

Data from a series of these experiments is summarized graphically in FIG. 5B. CFTR$_{inh}$-172 significantly reduced fluid secretion to that in saline control loops where an inactive thiazolidinone analog did not inhibit fluid secretion. As suggested from previous data (Gabriel et al. 1994 *Science* 266: 107-109), cholera toxin-treated loops of intestine from homozygous ΔF508-CFTR mice also remained empty, indicating the involvement of CFTR in intestinal fluid secretion. In the second assay, intestinal fluid secretion was induced by oral administration of cholera toxin (10 µg) and CFTR$_{inh}$-172 was administered systemically. After six hours there was marked accumulation of fluid as measured by weighing the entire small intestine. CFTR$_{inh}$-172 administration remarkably reduced intestinal fluid accumulation as seen visually and quantified by the ratio of intestinal weight before vs. after luminal fluid removal (FIG. 5C).

Figure 5D:
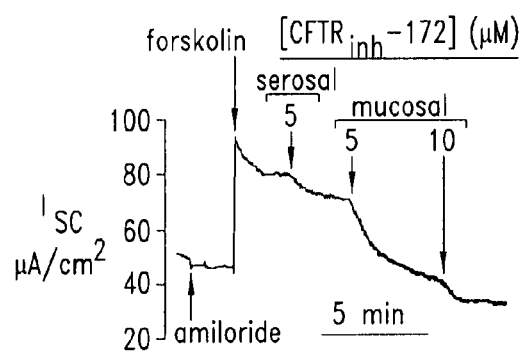
FIG. 5D is a graphical illustration showing a representative $CFTR_{inh}$-172 inhibition short-circuit current after amiloride addition and stimulation by forskolin (20 µM) in isolated rat colonic mucosa. $CFTR_{inh}$-172 added to serosal and then mucosal surfaces as indicated (n=4).

FIG. 5D shows CFTR$_{inh}$-172 inhibition of short-circuit current across intact rat colonic mucosa. After inhibition of Na$^+$ current by amiloride, forskolin produced a prompt increase in short-circuit current. CFTR$_{inh}$-172 added to the mucosal solution inhibited short-circuit current with greater efficacy than when added to the serosal solution, which may be related to impaired access to colonic epithelial cells through the residual submucosal tissue. Addition of 5 µM CFTR$_{inh}$-172 to the mucosal solution alone reduced short-circuit current by >80%. These results provide electrophysiological evidence for CFTR Cl$^-$ channel inhibition by CFTR$_{inh}$-172 in intestine.

Biological Example 4

Pharmacokinetic Analysis

Figure 7:
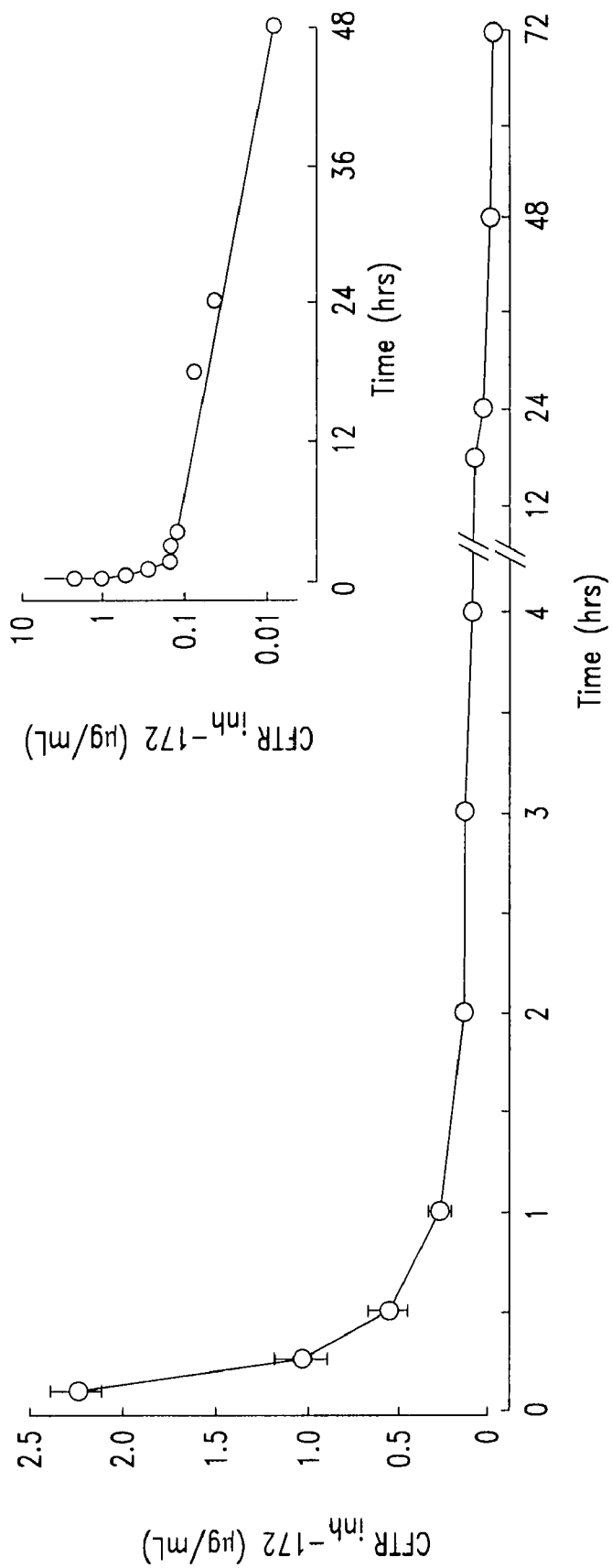
FIG. 7 is a set of graphs showing the results of pharmacokinetic analysis of $CFTR_{inh}$-172 in rats following a single intravenous bolus infusion of 50 µCi $^{14}$C-labeled $CFTR_{inh}$-172. Data shown as mean±SE (n=3-6 rats) for serum radioactivities. Fitted curve corresponds to a 2-compartment model with redistribution halftime 0.14 hr, elimination half-time 10.3 hr, maximum serum concentration 3.2 µg/mL, area-undercurve 3.8 µg·hr/mL, volume of distribution 1.2 L, and clearance 99 mL/hr.

Pharmacokinetic analysis in rats was done by serial measurements of serum $^{14}$C radioactivity after a single intravenous bolus infusion of $^{14}$C-labeled CFTR$_{inh}$-172. The total amount of inhibitor infused (400 µg, ~1 mg/kg) was effective as an antidiarrheal in rats. FIG. 7 shows that the kinetics of serum $^{14}$C radioactivity fitted well to a 2-compartment model with distribution volume 1.2 L and AUC (area under curve) of 3.8 µg hr/mL. The half-lives were 0.14 hr (redistribution) and 10.3 hr (elimination). No $^{14}$C-labeled CFTR$_{inh}$-4172 was detected in plasma at 72 hr after administration or in liver or kidney homogenates at 14 days after administration.

Figure 8A:
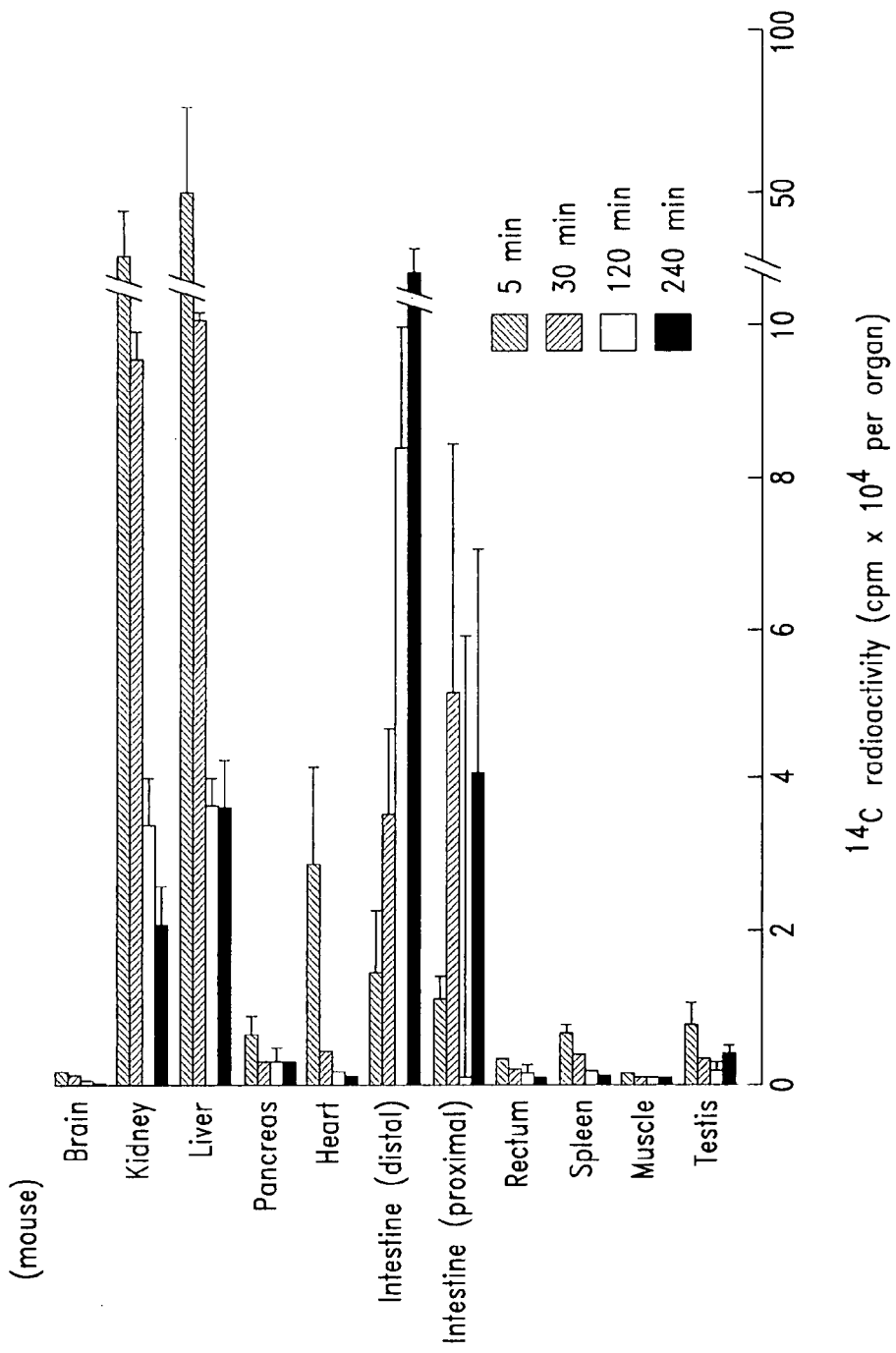
FIG. 8 is a set of graphs showing organ distribution of $^{14}$C-labeled $CFTR_{inh}$-172 after bolus infusion. The results in panel A are from mice given a single intravenous bolus infusion of 2 µCi $^{14}$C-labeled $CFTR_{inh}$-172, sacrificed at indicated times, and organs harvested for measurement of $^{14}$C-radioactivity, with data presented as total organ $^{14}$C-radioactivity at indicated times (except for skeletal muscle where reported as per gram tissue) after infusion (mean±SE, 4 mice per time point). The results in panel B are from rats given a bolus infusion of 50 µCi $^{14}$C-labeled $CFTR_{inh}$-172 and total organ $CFTR_{inh}$-172 measured at 60 min after infusion (3 rats).
Figure 8B:
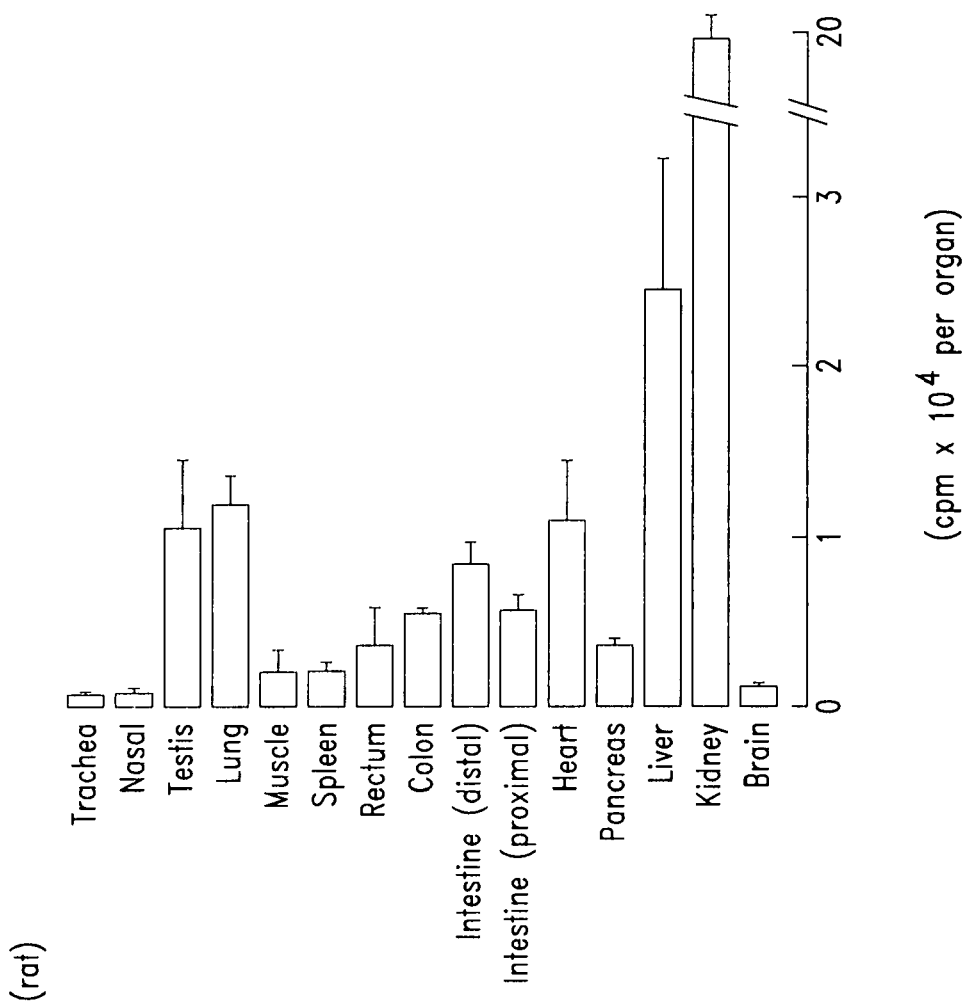

The tissue distribution of $^{14}$C-labeled CFTR$_{inh}$-172 was determined from the radioactivity of organ homogenates and bodily fluids following a single intravenous bolus infusion. FIG. 8, panel A summarizes $^{14}$C distributions in the major organs at indicated times after CFTR$_{inh}$-172 infusion in mice. $^{14}$C radioactivity was observed within 5 min primarily in liver and kidney, decreasing over time. Little radioactivity was found in brain, heart, skeletal muscle or testes. At later times (30-240 min) $^{14}$C radioactivity accumulated in the intestine. FIG. 3, panel B shows a similar organ distribution of $^{14}$C radioactivity in rats measured at 60 min after intravenous bolus infusion, with little radioactivity in brain, heart and skeletal muscle. In some experiments, rats were sacrificed at 10 days after infusion of $^{14}$C-labeled CFTR$_{inh}$-172 (50 µCi).

To determine the mechanism of CFTR$_{inh}$-172 accumulation in kidney, liver and intestine, $^{14}$C radioactivity was measured in serum, urine and bile. Average urine radioactivity was 4.2±1.2×10$^5$ cpm/mL in mice over the first 2 hours after infusion. The ratios of $^{14}$C radioactivity in urine-to-blood were in the range 5-7:1, comparable to the ratio of urine-to-serum osmolarities of ~5:1 (1550 mOsm vs. 310 mOsm), suggesting that CFTR$_{inh}$-172 is cleared by the kidney by glomerular filtration without renal tubular absorption or secretion. A renal clearance mechanism for CFTR$_{inh}$-172 clearance was supported by the approximately parallel kinetics of decreasing $^{14}$C radioactivity in serum, urine and kidney tissue (data not shown). The possibility of CFTR$_{inh}$-172 accumulation in bile was investigated based on the observation of prompt accumulation of $^{14}$C-radioactivity in liver and late accumulation in intestine. $^{14}$C radioactivity was ~9-fold concentrated in bile vs. blood at 60 min after administration in mice. To determine whether the biliary CFTR$_{inh}$-172 was excreted in the stool or returned to the circulation, urine and stool collections were done on mice over the first 24 hr after radiolabeled inhibitor infusion. 93±3% of excreted radioactivity was found in the urine, supporting a primary renal excretion mechanism with enterohepatic circulation.

Figure 9:
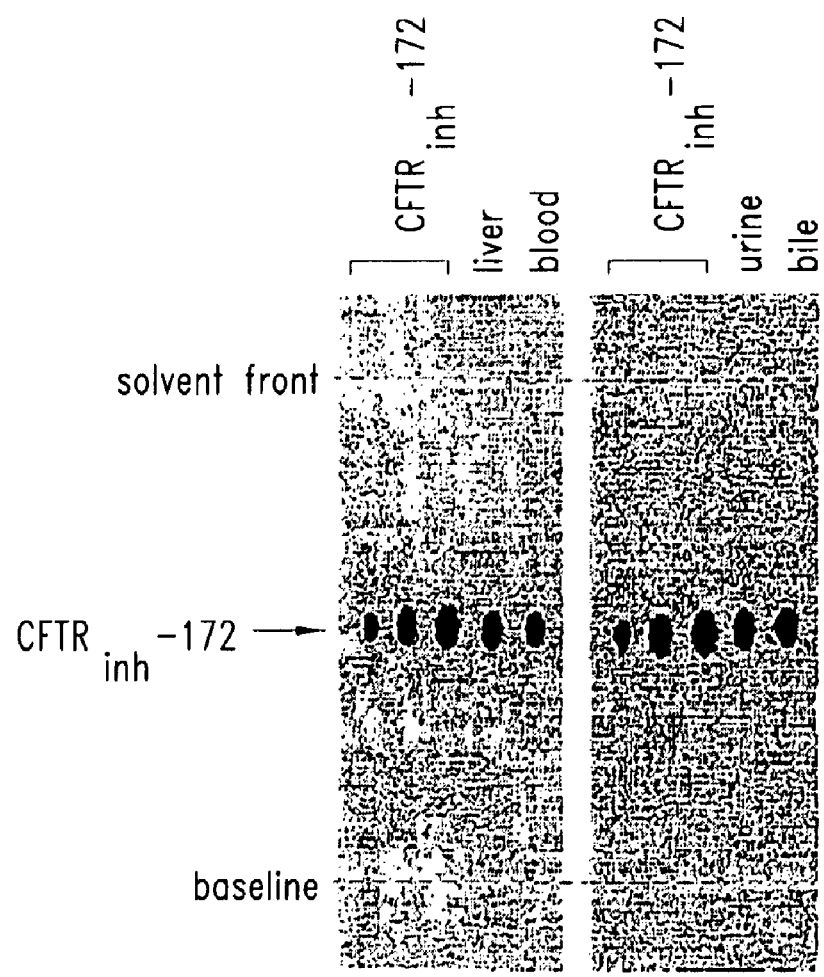
FIG. 9 is a set of photographs showing the results of analysis of $CFTR_{inh}$-172 metabolism by thin layer chromatography of fluids and liver homogenate from mice infused with $^{14}$C-labeled $CFTR_{inh}$-172 as in FIG. 8, panel A. $^{14}$C-$CFTR_{inh}$-172 standards were 1, 3 and 6 nCi (left panel), and 10, 30 and 60 nCi (right panel). Film was exposed for autoradiography for 48 hr (left panel) and 12 hr (right panel).

To determine whether the $^{14}$C radioactivity measured in organs and fluids corresponds to intact or chemically-modified CFTR$_{inh}$-172, thin layer chromatography and autoradiography were done on specimens of urine, serum and bile, as well as supernatants of liver homogenates prepared by centrifugation. FIG. 9 shows a single spot at rf ~0.5 for the original CFTR$_{inh}$-172 introduced in the bolus infusion. Autoradiography of fluid and organ homogenates showed single spots at identical rf, indicating that chemical modification of CFTR$_{inh}$-172 did not occur.

CFTR$_{inh}$-172 is a weak acid with a pKa of 5.5 as determined by spectrophotometric pH titration. At physiological pH ~1% of CFTR$_{inh}$-172 is present as the unionized acid having low polarity and high membrane permeability. The rapid uptake of CFTR$_{inh}$-172 in cell models described above suggests the feasibility of orally bioavailable preparations with the caveat that protection from the low gastric pH may be needed to avoid precipitation. The results from these pharmokinetic studies indicate that CFTR$_{inh}$-172 is slowly eliminated in rodents by renal clearance without chemical modification, and that CFTR$_{inh}$-172 is concentrated in bile and accumulated in intestine. CFTR$_{inh}$-172 did not significantly cross the blood-brain barrier and little CFTR$_{inh}$-172 accumulation was found in other vital organs including heart, lung, skeletal muscle and testes. The slow renal clearance, intestinal accumulation, and little blood-brain barrier penetration of CFTR$_{inh}$-172 are favorable for antidiarrheal applications.

Biological Example 5

Dose-Response and Duration of Inhibitory Effect of CFTR$_{inh}$-172

The purpose of this example was to extend the observations above relating to the ability of a single intraperitoneal injection of CFTR$_{inh}$-172 to inhibit cholera toxin-stimulated fluid secretion in a closed intestinal loop model in mice. Specifically, the goal of this example was to measure the dose-response relation and the apparent halftime for persistence of the CFTR$_{inh}$-172 inhibitory effect.

Figure 10A:
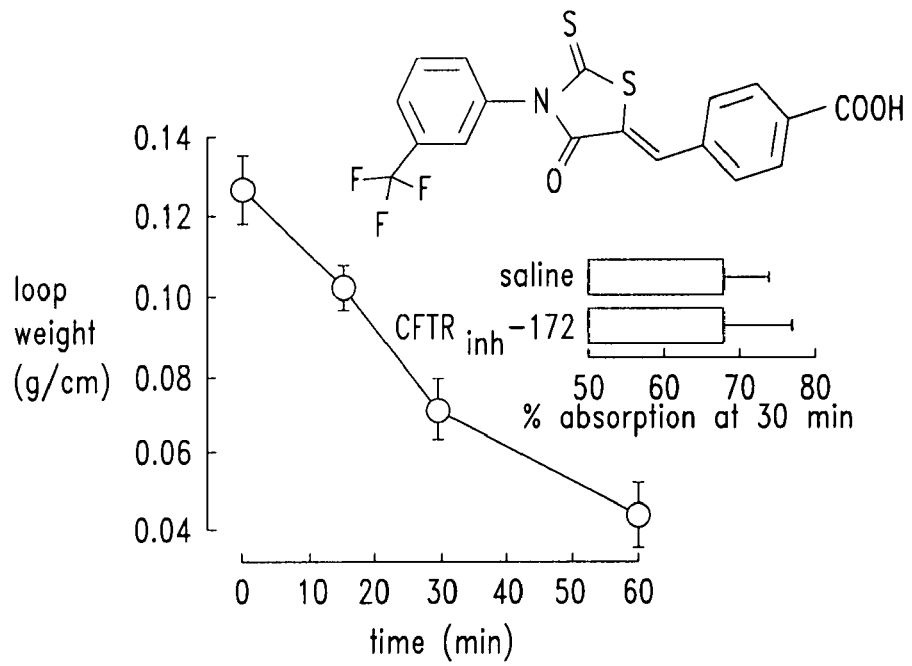
FIG. 10 is a set of graphs providing the results of characterization of the mouse closed-intestinal loop model. Panel A: Intestinal loops were injected with 200 µL buffer and loop weight measured at indicated times (mean±SEM, 4 mice per time point). Inset (lower) % absorption at 30 min with and without $CFTR_{inh}$-172 (20 µg I.P., n=4). Inset (top) Chemical structure of $CFTR_{inh}$-172. Panel B: Time course of cholera toxin-induced fluid secretion in mouse closed-loop model. Dashed line shows control (saline-injected) loops. Data for injected loops (1 µg cholera toxin/loop) as mean±SEM (4-6 mice).
Figure 10B:
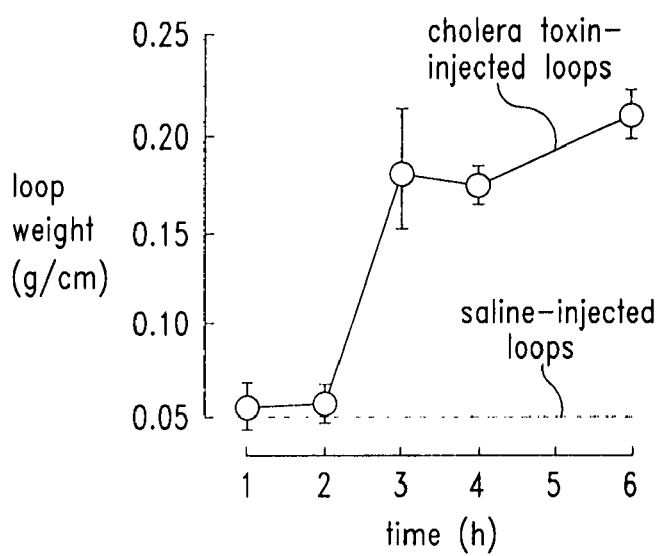

First, the kinetics of intestinal loop fluid absorption and secretion were determined to characterize the mouse model. To study absorption, loop fluid content was measured at specified times after injection of 200 μL of PBS into individual loops. FIG. 10, panel A shows rapid fluid absorption with 50% fluid remaining at ~25 min. Intraperitoneal administration of CFTR$_{inh}$-172 at a dose that strongly inhibited cholera toxin-induced intestinal fluid secretion (20 μg) did not alter the rate of fluid absorption (measured at 30 min) compared to controls (FIG. 10, panel A, inset). To study secretion, intestinal loops were injected with cholera toxin (1 μg in 0.1 mL PBS). FIG. 10, panel B shows a slow onset of fluid secretion over 6 hr, in agreement with previous studies in rodent models (Gorbach et al. *J. Clin. Invest.* 1971 50-881-889; Oi et al. *Proc. Natl. Acad. Sci.* USA 2002 99:3042-3046). The rapid absorption of fluid in the intestine under normal conditions suggests that fluid accumulated in the intestinal lumen after active secretion may be absorbed rapidly if secretion is blocked, predicting that CFTR inhibition could be effective in preventing fluid accumulation even when administered after cholera toxin.

Figures 11C, 11D:
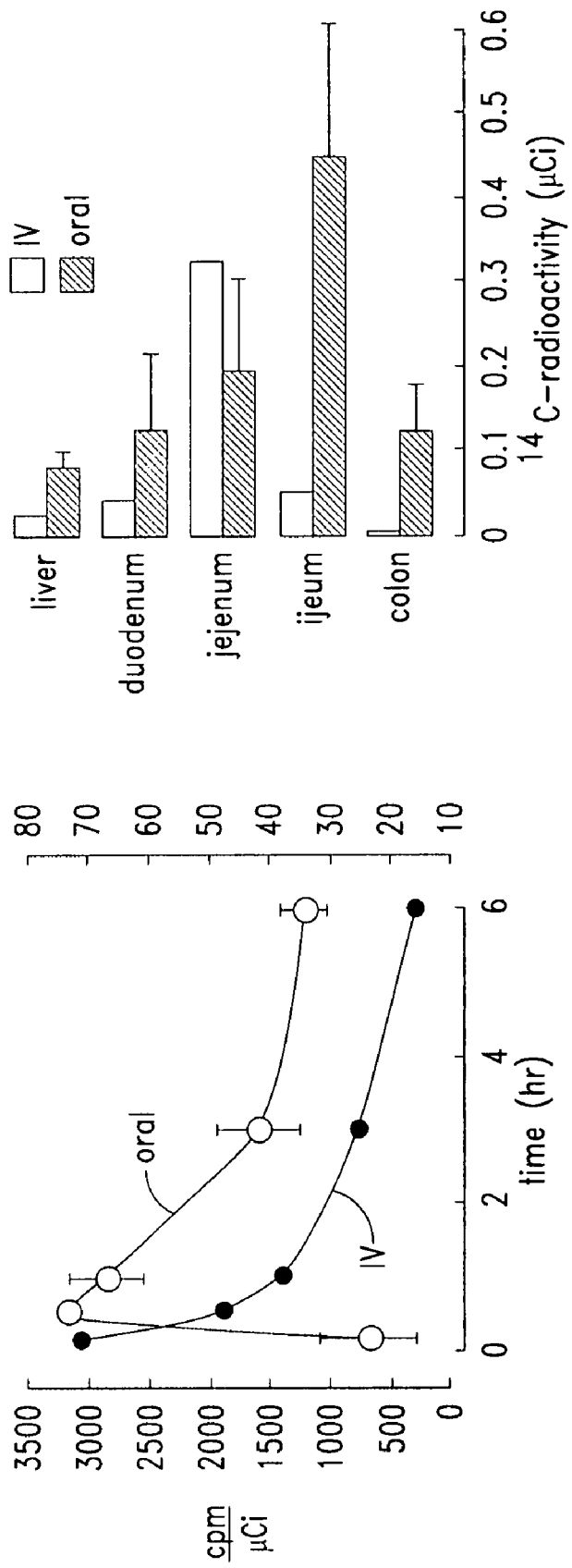
FIG. 11 is a set of graphs showing $CFTR_{inh}$-172 inhibition of intestinal fluid secretion after cholera toxin in mice. Panel A: Dose-response for inhibition of fluid accumulation in mouse loop model. Mice were given single doses of $CFTR_{inh}$-172 by intraperitoneal injection and loop weight (mean±SEM, 4-6 mice per dose) measured at 6 hr. Dashed line indicates average weight in saline-injected control loops of same mice. Panel B: Persistence of $CFTR_{inh}$-172 inhibition. Mice were injected with 20 μg $CFTR_{inh}$-172 (I.P.) at indicated times before or after cholera toxin administration (4-6 mice per time point). Panel C: Time course of plasma $^{14}C$-$CFTR_{inh}$-172 radioactivity after i.v injection (tail vein, left ordinate) and oral administration ($CFTR_{inh}$-172 in TPGS, right ordinate). Data shown as counts per min per μCi injected (4 mice). Panel D: $^{14}C$-$CFTR_{inh}$-172 accumulation in gastrointestinal organs at 6 hr after i.v. and oral $^{14}C$-$CFTR_{inh}$-172 administration (4 mice). Panel E: Inhibition of cholera toxin-induced fluid secretion by orally-administered $CFTR_{inh}$-172 (200 μg in TPGS) in mouse open-loop model. Data shown as ratio of weight of entire small intestine 6 hr after oral gavage before vs. after luminal fluid removal (mean±SEM, 4 mice per group, * $p<0.01$). Panel F: $CFTR_{inh}$-172 permeability across Caco-2 monolayers (mean±SEM, 18 inserts) with Papp=$16\times10^{-6}$ cm/s.
Figures 11E, 11F:
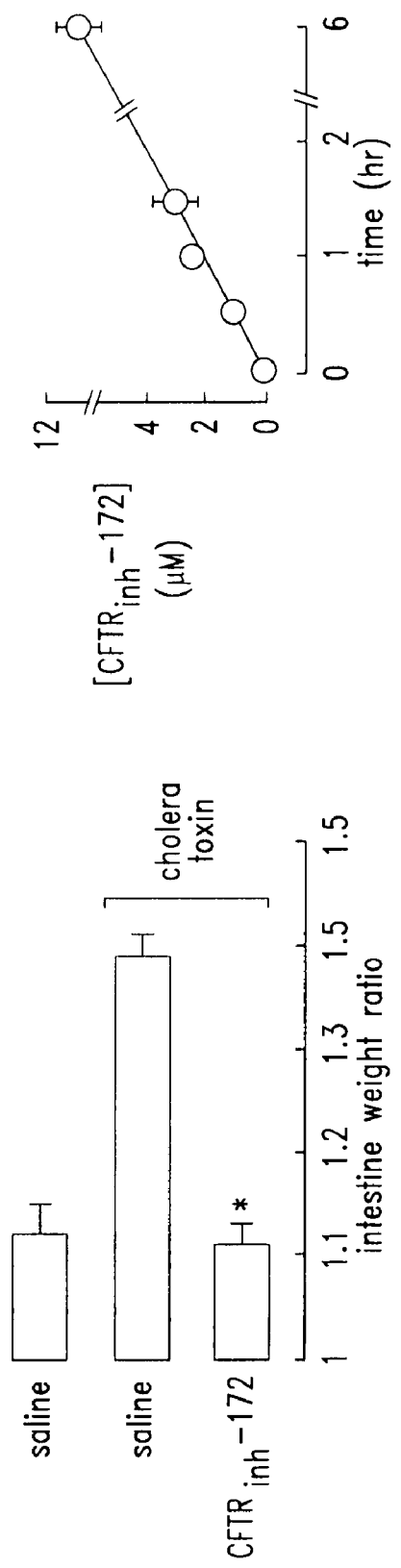

FIG. 11, panel A summarizes the results of a CFTR$_{inh}$-172 dose-response study in mice in which a single dose of inhibitor was administered by intraperitoneal injection just after infusion of cholera toxin into closed intestinal loops. Basal intestinal fluid content (dashed line) was near zero as measured in non-cholera toxin injected loops. CFTR$_{inh}$-172 inhibited fluid accumulation in cholera toxin-injected intestinal loops by ~90%, with 50% inhibition at ~5 μg CFTR$_{inh}$-172 (150 μg/kg). The duration of inhibition was measured as in the dose-response study, except that a single 20 μg dose of CFTR$_{inh}$-172 was administered at different times before or after cholera toxin. FIG. 11, panel B shows significant inhibition of luminal fluid accumulation when CFTR$_{inh}$-172 was administered at 3 hr before or after cholera toxin. However much less inhibition was seen at 6 hr before cholera toxin. Taking into account the 6 hr duration of the cholera toxin challenge study, the $t_{1/2}$ for persistence of CFTR$_{inh}$-172 inhibition was ~9-10 hr.

Biological Example 6

Oral Bioavailability of CFTR$_{inh}$-172

To test the antidiarrheal efficacy of orally administered CFTR$_{inh}$-172, CFTR$_{inh}$-172 pharmacokinetics in mice was determined, and CFTR$_{inh}$-172 transport across Caco-2 monolayers was measured. Because CFTR$_{inh}$-172 is a relatively nonpolar weak acid (pKa 5.5) expected to precipitate in the stomach, oral administration was done using two agents used commonly to solubilize drugs for oral administration—Vitamin E TPGS and cyclodextrin. Measurements were done using $^{14}$C-labeled CFTR$_{inh}$-172.

FIG. 11, panel C shows the pharmacokinetics of $^{14}$C-CFTR$_{inh}$-172 after oral vs. intravenous administration in mice. Intravenous administration produced high initial serum concentrations that decreased over ~30 min (tissue redistribution), whereas serum radioactivity was low just after oral administration, peaked at ~60-90 min, and then declined.

FIG. 11, panel D summarizes the organ distribution of $^{14}$C-CFTR$_{inh}$-172 at 6 hr after oral and intravenous administration, showing accumulation in the gastrointestinal tract as well as the liver and kidney. $^{14}$C radioactivity was concentrated ~10-fold in bile vs. serum, with little radioactivity excreted in the stool (<10% of total excreted radioactivity over 24 hr), suggesting that accumulation of CFTR$_{inh}$-172 in intestine is facilitated by enterohepatic circulation. Comparison of oral vs. intravenous CFTR$_{inh}$-172 administration (tissue/serum content at 4-6 hr) indicated 15-20% CFTR$_{inh}$-172 oral bioavailability in the TPGS preparation.

FIG. 11, panel F shows a linear increase in the appearance of CFTR$_{inh}$-172 on the trans-side of Caco-2 monolayers, giving a deduced CFTR$_{inh}$-172 permeability coefficient of $16 \times 10^{-6}$ cm/s. This value is in the range found for various orally-administered drugs (e.g. pindolol, $36 \times 10^{-6}$ cm/s, sildenafil, $48 \times 10^{-6}$ cm/s) (Stenberg et al. *J. Med. Chem.* 2001 44:1927-1937.

Biological Example 7

Inhibition of cGMP- and cAMP-Mediated Fluid Secretion

Figure 12B:
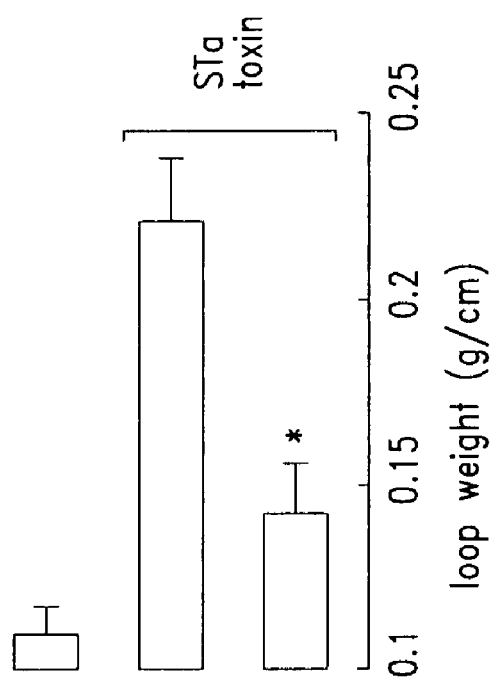
FIG. 12 is a set of graphs showing $CFTR_{inh}$-172 inhibition of cholera toxin (Panel A) and STa toxin (Panel B) induced fluid secretion in rat closed-loop model. Data shown as mean±SEM (4 rats per group), * $p<0.01$.
Figure 12A:
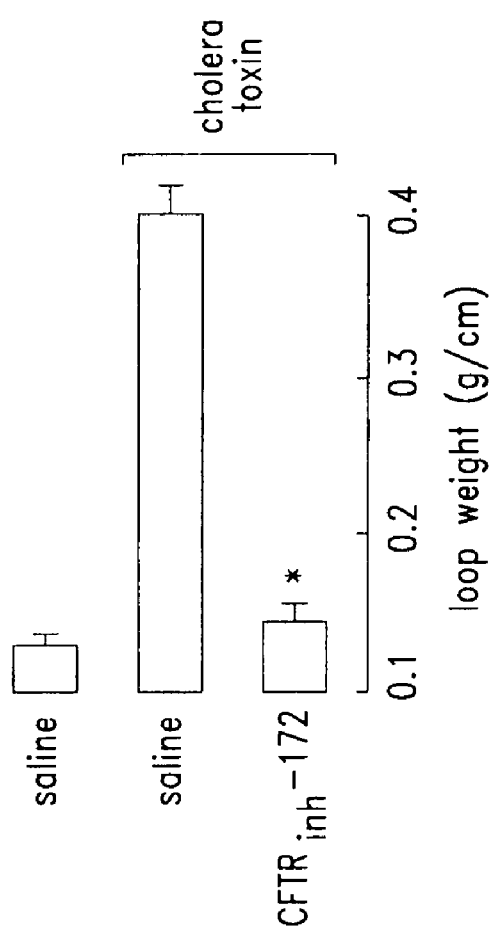

An in vivo rat intestinal loop model was used to determine the efficacy of CFTR$_{inh}$-172 in inhibiting cGMP- and cAMP-mediated fluid secretion, as well as to test the efficacy of CFTR$_{inh}$-172 in an alternative animal model. The guanylyl cyclase C receptor is expressed in rat enterocytes, permitting STa toxin binding and cytoplasmic cGMP elevation (Mann et al. *Biochem Biophys Res commun* 1997 239:463-466). STa toxin has been found to cause fluid secretion in rat ileum after 3 hr (Cohen et al *Am J Physiol* 1989 257:G118-123). CFTR$_{inh}$-172 prevented cholera-toxin induced fluid secretion in rat intestinal loops (FIG. 12, panel A) at a dose (600 μg/kg) that was effective in mice. For STa toxin-induced fluid secretion intestinal loops were injected with STa toxin (0.1 μg in 300 μL PBS) and loop weight measured after 3 hr. FIG. 12, panel B shows ~75% inhibition of intestinal fluid secretion by CFTR$_{inh}$-172.

Figures 13A, 13B:
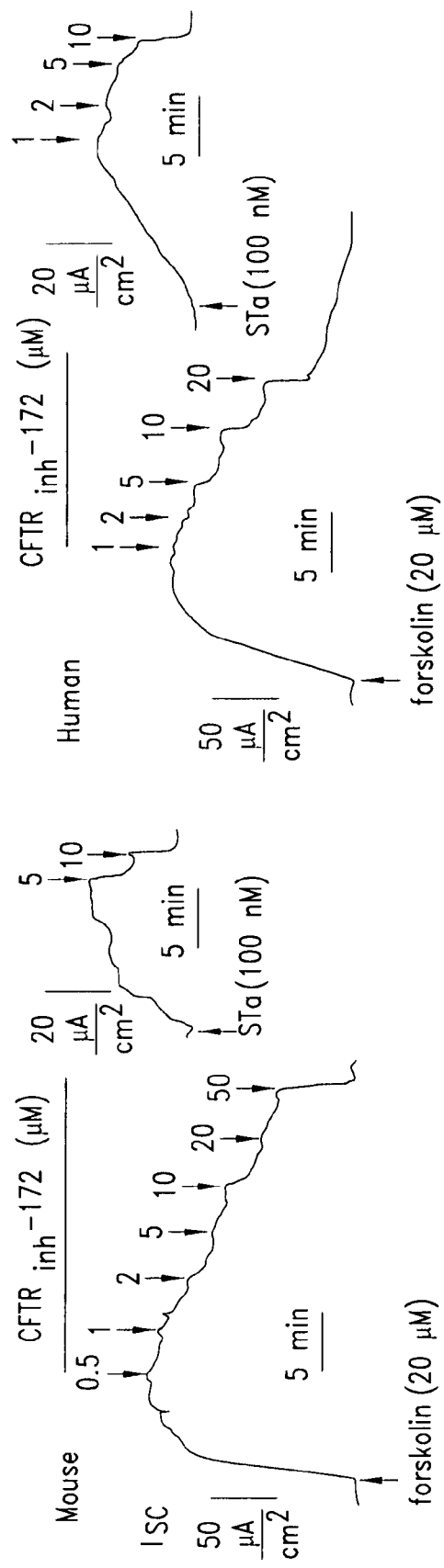
FIG. 13 is a set of graphs showing $CFTR_{inh}$-172 inhibition of forskolin- and STa toxin-stimulated short-circuit current in mouse ileum (Panel A) and human colon (Panel B). STa toxin shown as inset. Data are representative of studies of 5 mice and 2 sets of human tissues. $CFTR_{inh}$-172 added to both sides of tissue. Amiloride (10 μM) was present in the apical solutions.

Short-circuit current measurements were done in mouse and human intestinal epithelial sheets to assess CFTR$_{inh}$-172 inhibition of transepithelial ion secretion. FIG. 13, panel A shows CFTR$_{inh}$-172 dose-dependent inhibition of short-circuit current in mouse ileum after stimulation by forskolin or STa toxin (inset). Fifty percent inhibition was found at ~5 μM CFTR$_{inh}$-172 for both cAMP and cGMP-dependent chloride secretion. FIG. 12, panel B shows similar CFTR$_{inh}$-172 potency for inhibition of short-circuit current in human colon.

An unexpected observation was that the apparent potency for CFTR$_{inh}$-172 inhibition of intestinal short-circuit current (2-5 μM) was substantially lower than that found in electrophysiological studies done on several cell lines including CFTR-expressing FRT cells (0.2-0.5 μM) and Calu-3 cells (0.5 μM). Several explanations for this difference were considered, including cell-type differences, limited access of CFTR$_{inh}$-172 to enterocytes in intact intestine, membrane potential effects (interior-negative cell potential reducing intracellular [CFTR$_{inh}$-172]), and ATP competition with CFTR$_{inh}$-172.

Figure 14A:
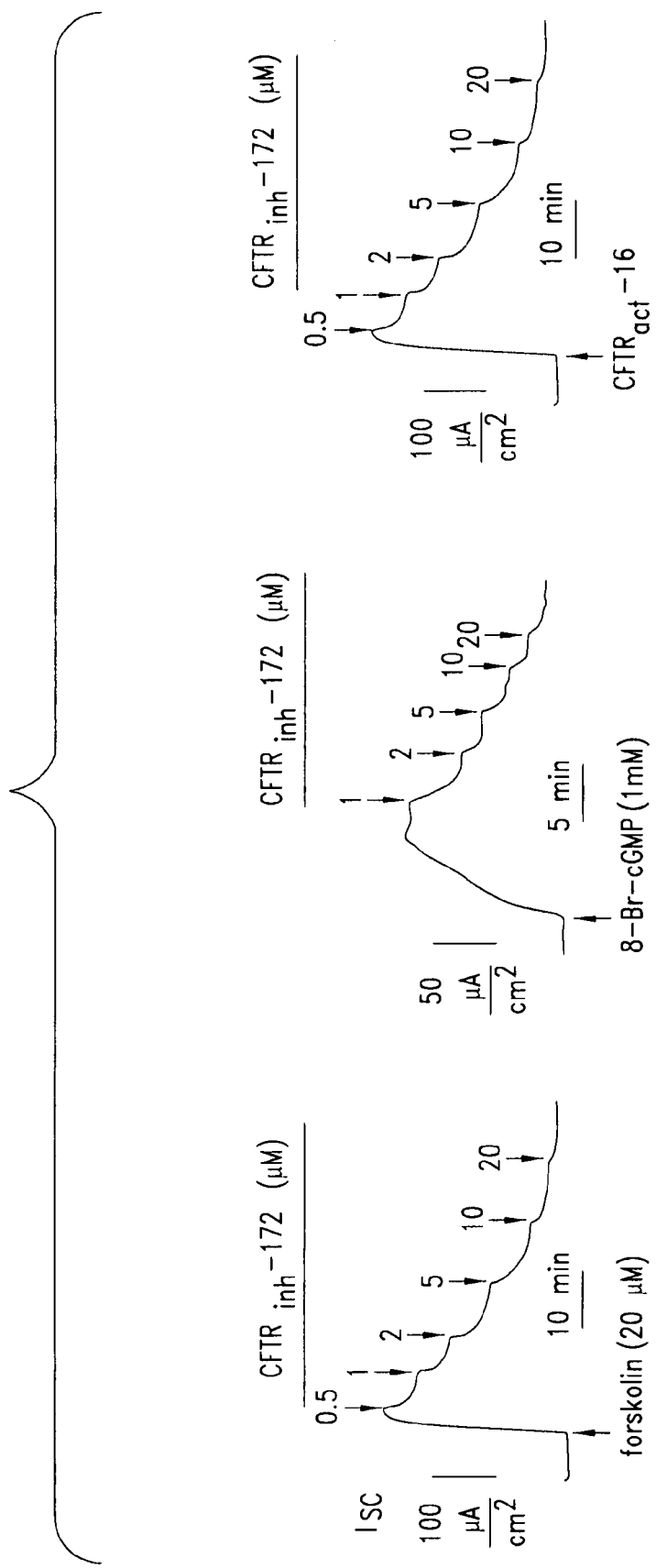
FIG. 14 is a set of graphs showing short-circuit analysis of $CFTR_{inh}$-172 inhibition of $Cl^-$ secretion in T84 colonic epithelial cells. Panel A: Data shown as representative traces from experiments on 5-12 inserts per condition. $CFTR_{inh}$-172 added to both sides of cell layers. CFTR agonists include forskolin (left), 8-Br-cGMP (middle), and $CFTR_{act}$-16 (right). Panel B: (left) $CFTR_{inh}$-172 inhibition of forskolin-stimulated short-circuit current after basolateral permeabilization with amphotericin B (250 μg/mL). Representative of experiments on 6 inserts. (middle) Average dose-response for $CFTR_{inh}$-172 inhibition of forskolin-stimulated (circles) and 8-Br-cGMP-stimulated (triangles) short-circuit current in permeabilized vs. non-permeabilized T84 cells (mean±SEM, 6-12 inserts). (right) $CFTR_{inh}$-172 inhibition of forskolin-stimulated short-circuit current in the presence of high $K^+$ (68 mM) in the basolateral solution with low $Cl^-$ in the apical solution. Representative of 4 experiments.
Figure 14B:
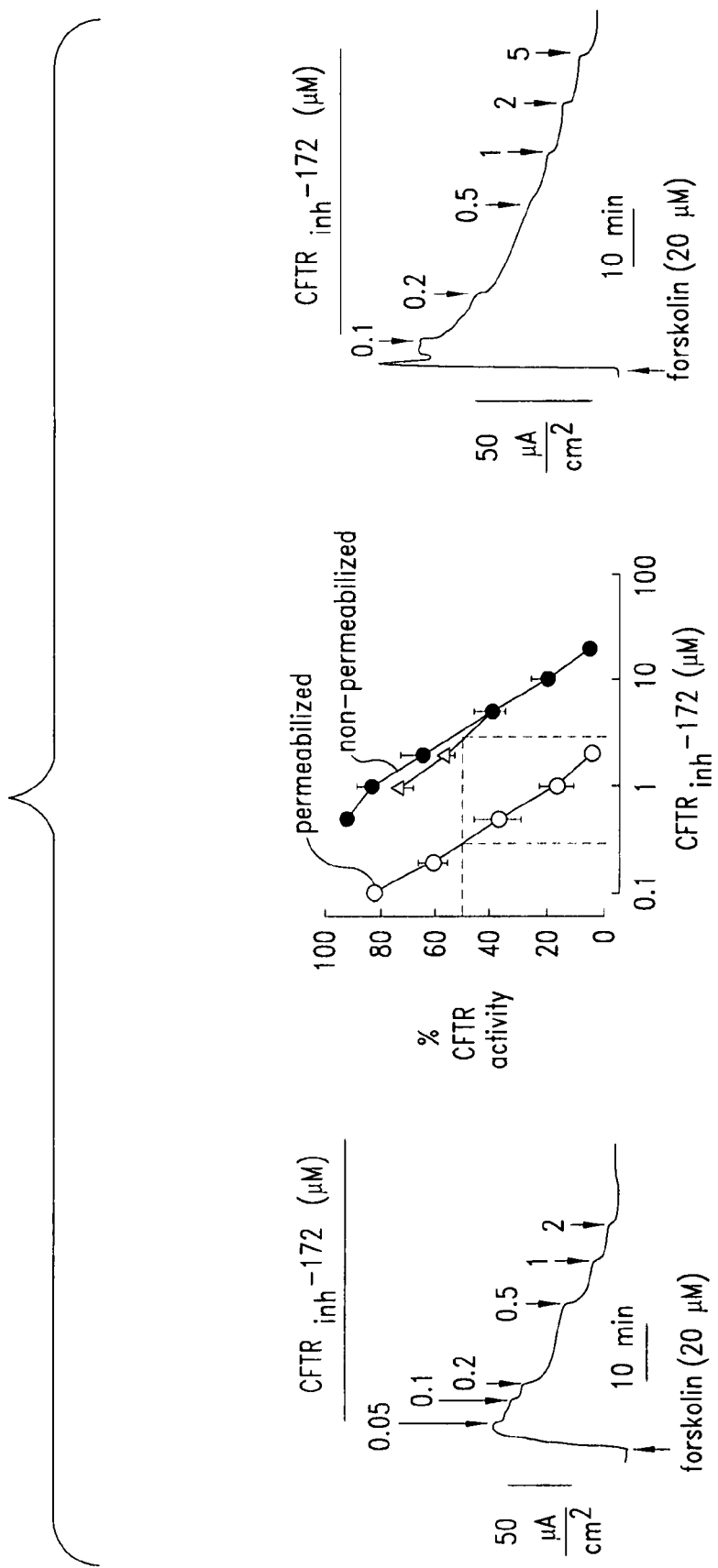

Short-circuit current measurements were done on T84 colonic epithelial cells to investigate this phenomenon. As shown in representative experiments in FIG. 14, panel A, ~3

μM CFTR$_{inh}$-172 produced 50% inhibition of short-circuit current in non-permeabilized T84 cell monolayers after stimulation by the cAMP agonist forskolin (left), the cell permeable cGMP analog 8-Br-cGMP (middle), or the direct activator of CFTR chloride conductance CFTR$_{act}$-16 identified by high throughput screening. To determine whether the relative reduction in CFTR$_{inh}$-172 potency in T84 cells requires an intact cell, short-circuit current measurements were done after permeabilizing the cell basolateral membrane with amphotericin B and in the presence of a Cl$^-$ gradient (to generate measurable currents). FIG. 14, panel B (left) shows substantially greater CFTR$_{inh}$-172 potency for inhibition of short-circuit current after permeabilization. Dose-response data summarized in FIG. 14, panel B (middle) indicate a reduction in apparent KI for CFTR$_{inh}$-172 inhibition from ~3 to 0.3 μM after cell permeabilization. To test whether the reduced CFTR$_{inh}$-172 potency in intact cells is due to the interior-negative membrane potential (reducing cytoplasmic vs. external [CFTR$_{inh}$-172]), short circuit current measurements were done in T84 cells after depolarization by a high-K$^+$ basolateral bathing solution. FIG. 14, panel C shows that increased CFTR$_{inh}$-172 potency (KI ~0.3 μM) was restored in the depolarized cells, indicating that cell membrane potential plays a role in CFTR$_{inh}$-172 potency.

Based on the data above, the thiazolidine compounds of the invention, as exemplified by CFTR$_{inh}$-172, can be expected to have antidiarrheal efficacy in enterotoxin induced secretory diarrheas caused by enterotoxigenic organisms such as *E. coli* and *Vibrio cholerae* in cholera, Traveller's and AIDS-complex related diarrheas. CFTR inhibition may be useful in adjunct therapy of diarrheas caused by entero-invasive bacterias such as *Clostridium difficile* and *Salmonella* species; however, the mucosal damage produced by these organisms would not be reduced by CFTR inhibition. Similarly, CFTR inhibition would not be predicted to correct the underlying pathology in inflammatory bowel disease, but could reduce the volume of intestinal fluid secretions. Recent evidence suggests that fluid secretion caused by viral diarrheas such as rotavirus may involve other mechanisms such as Ca$^{2+}$-mediated Cl$^-$ channels, although the role of CFTR in fluid secretions remains unknown and hence testable by use of the compounds of the invention in suitable animal models.

In summary, the thiazolidinone CFTR blocker CFTR$_{inh}$-172 prevented cAMP and cGMP induced ion/fluid secretion in rodent and human intestine without affecting intestinal fluid absorption. Its favorable pharmacological and activity profile support further development for antidiarrheal applications.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A pharmaceutical composition comprising a compound of formula (Ib):

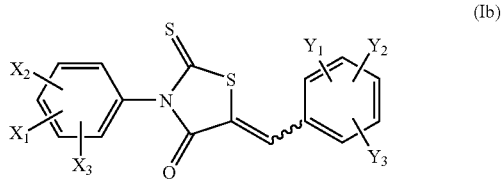

(Ib)

wherein X$_1$ is trifluoromethyl; X$_2$ and X$_3$ are independently chosen from hydrogen and a halo group; Y$_1$, Y$_2$ and Y$_3$ are independently chosen from hydrogen, C$_1$-C$_8$ alkyl, C$_1$-C$_7$ alkoxy, carbonate, carbamate, carboxyl, a halo group, a nitro group, an azo group, a hydroxyl group and a mercapto group and at least one of a pharmaceutically acceptable carrier, a pharmaceutically acceptable diluent, and a pharmaceutically acceptable excipient.

2. The composition of claim 1, wherein X$_1$ is located at the 2, 3, or 4 position of the phenyl group to which it is attached.

3. The composition of claim 1, wherein Y$_2$ is chosen from hydroxyl, carboxyl, nitro, carbonate, and a halo group.

4. The composition of claim 1, wherein X$_1$ is a 3-trifluoromethyl group.

5. The composition of claim 1, wherein Y$_2$ is a hydroxyl group.

6. The composition of claim 5, wherein Y$_1$ is a hydroxyl group or a bromo group.

7. The composition of claim 5, wherein Y$_3$ is a nitro group.

8. The composition of claim 1, wherein the compound is a compound of formula (Ic):

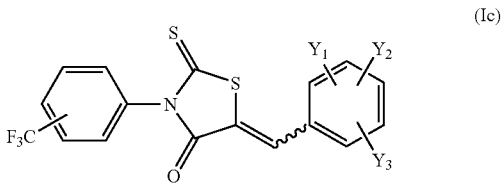

(Ic)

wherein Y$_1$, Y$_2$ and Y$_3$ are independently chosen from hydrogen, carbonate, carboxyl, a halo group, a nitro group, and a hydroxyl group.

9. The composition of claim 8, wherein the trifluoromethyl group is located at the 2, 3, or 4 position of the phenyl group to which it is attached.

10. The composition of claim 8, wherein the trifluoromethyl group is located at the 3-position.

11. The composition of claim 8 wherein Y$_2$ is hydroxyl.

12. The composition of claim 11 wherein Y$_1$ is a hydroxyl group or a bromo group.

13. The composition of claim 11 wherein Y$_3$ is a nitro group.

* * * * *